(«12») United States Patent
Eguchi

(10) Patent No.: US 12,023,194 B2
(45) Date of Patent: Jul. 2, 2024

(54) RADIOGRAPHY APPARATUS

(71) Applicant: FUJIFILM CORPORATION, Tokyo (JP)

(72) Inventor: Koichi Eguchi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 297 days.

(21) Appl. No.: 17/718,272

(22) Filed: Apr. 11, 2022

(65) Prior Publication Data

US 2022/0233161 A1    Jul. 28, 2022

Related U.S. Application Data

(63) Continuation of application No. PCT/JP2020/039422, filed on Oct. 20, 2020.

(30) Foreign Application Priority Data

Oct. 31, 2019    (JP) ................................. 2019-199330

(51) Int. Cl.
*A61B 6/00*    (2024.01)

(52) U.S. Cl.
CPC .............. *A61B 6/56* (2013.01); *A61B 6/4441* (2013.01)

(58) Field of Classification Search
CPC ........ A61B 6/4405; A61B 6/4441; A61B 6/56
See application file for complete search history.

(56) References Cited

U.S. PATENT DOCUMENTS

| 4,328,659 A | 5/1982 | Seyerle |
| 5,980,107 A * | 11/1999 | Kusch .................... H02G 11/02 439/4 |
| 6,609,826 B1 | 8/2003 | Fujii et al. |
| 2008/0087871 A1 | 4/2008 | Schena |

FOREIGN PATENT DOCUMENTS

| JP | H07-265287 A | 10/1995 |
| JP | H08-229027 A | 9/1996 |
| JP | 2002-34960 A | 2/2002 |
| JP | 3154652 U | 10/2009 |
| WO | 2001/010300 A1 | 2/2001 |

OTHER PUBLICATIONS

International Search Report issued in International Application No. PCT/JP2020/039422 on Dec. 15, 2020.
Written Opinion of the ISA issued in International Application No. PCT/JP2020/039422 on Dec. 15, 2020.

\* cited by examiner

*Primary Examiner* — Dani Fox
(74) *Attorney, Agent, or Firm* — SOLARIS Intellectual Property Group, PLLC

(57) ABSTRACT

A radiography apparatus includes: an arm that has a first end portion and a second end portion, one of which an irradiator is provided in and the other of which an image receiver is attachable to; a support portion that supports the arm to be orbitally rotatable; a cable that is provided from the first end portion of the arm to the support portion; a belt that is provided from the second end portion of the arm to the support portion; a first reel that winds the cable; a second reel that is provided to be independently rotatable with respect to the first reel and winds the belt; and a spring that biases the first reel in a winding direction of the cable, biases the second reel in a winding direction of the belt, and allows the occurrence of a difference between an amount of rotation of the first reel and an amount of rotation of the second reel.

12 Claims, 18 Drawing Sheets

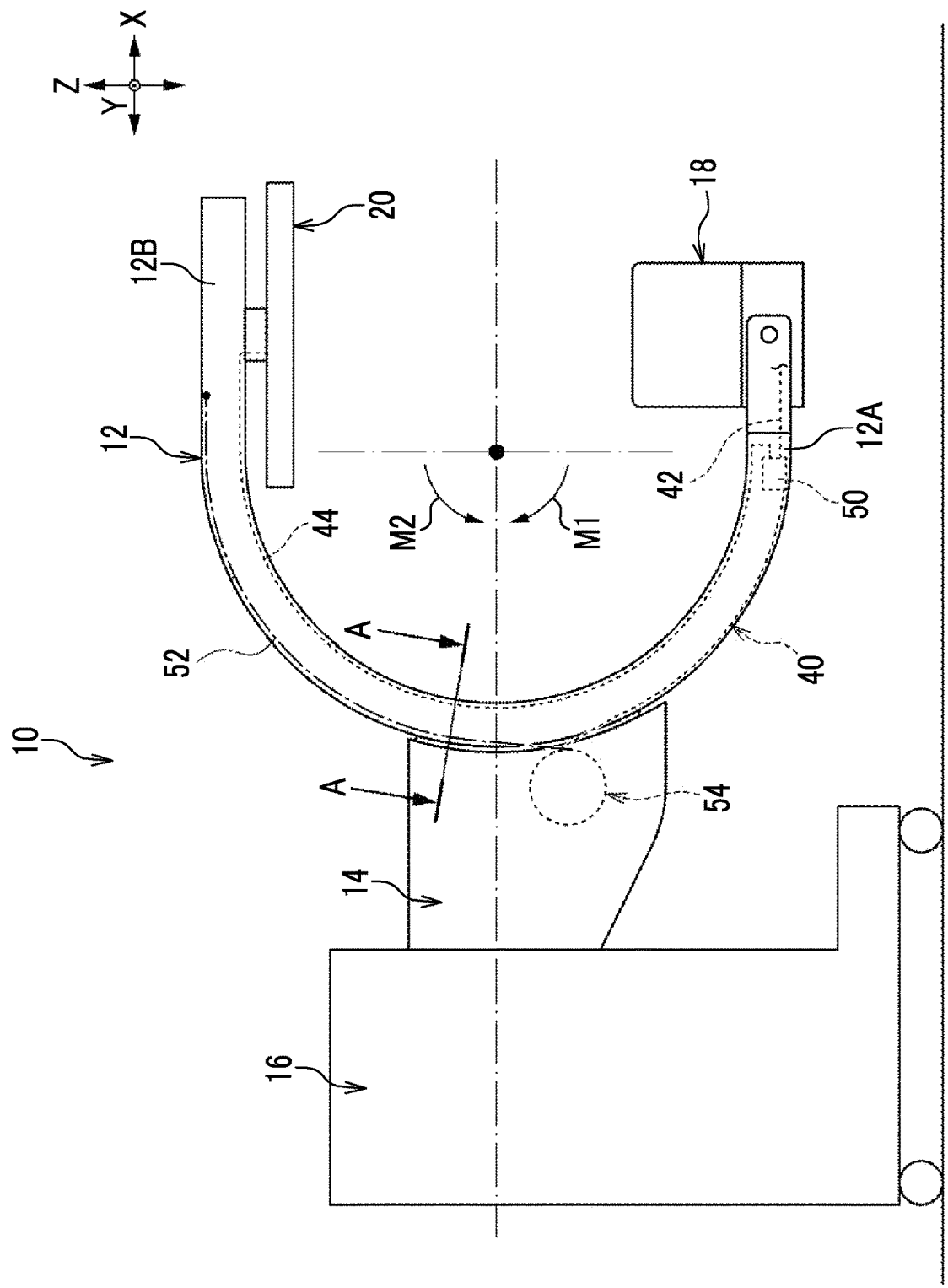

RADIOGRAPHY APPARATUS

CROSS-REFERENCE TO RELATED APPLICATIONS

This application is a continuation application of International Application No. PCT/JP2020/039422, filed Oct. 20, 2020, the disclosure of which is incorporated herein by reference in its entirety. Further, this application claims priority from Japanese Patent Application No. 2019-199330, filed on Oct. 31, 2019, the disclosure of which is incorporated herein by reference in its entirety.

BACKGROUND

1. Technical Field

The present disclosure relates to a radiography apparatus.

2. Description of the Related Art

A radiography apparatus is known which includes an arm having two end portions of a first end portion and a second end portion, one of which an irradiation unit that emits radiation is provided in and the other of which an image receiving unit that receives the radiation emitted from the irradiation unit and transmitted through a subject is attachable to (see JP1996-229027A (JP-H08-229027A)). The arm has an arc shape in a side view and is called, for example, a C-arm.

This arm can be orbitally rotated around the subject in a posture in which the irradiation unit and the image receiving unit face each other. The arm is supported by a support portion that has a track portion fitted to an arc-shaped outer peripheral portion of the arm. In a case in which the outer peripheral portion of the arm is moved along the track portion, the arm is orbitally rotated about the center of the arc shape as the center of rotation.

In addition, the arm is provided with a cable that is used for electrical connection to each of the irradiation unit and the image receiving unit. The cable is provided in the outer peripheral portion of the arm and is drawn into the support portion. For example, in a case in which the cable is provided from the first end portion of the arm to the support portion, the length of the cable is determined according to the rotation range of the orbital rotation of the arm. The maximum length of the cable from the support portion to the first end portion of the arm is the length to a position where the first end portion is farthest from the support portion. Therefore, in a case in which the arm is orbitally rotated in a first direction in which the first end portion approaches the support portion, the cable is loosened by the amount of movement the first end portion to the support portion. In a case in which the cable is loosened, a loosened portion interferes with work. Therefore, it is necessary to take measures to suppress the loosening of the cable.

In order to solve this problem, for example, the radiography apparatus (X-ray apparatus) disclosed in JP1996-229027A (JP-H08-229027A) comprises a winding drum that winds the cable (electric wire), a pulley that can be coaxially rotated integrally with the winding drum, and a wire that is wound around the pulley and applies tension to the cable.

According to the radiography apparatus disclosed in JP1996-229027A (JP-H08-229027A), in a case in which the arm is orbitally rotated, the wire is unwound from the pulley to rotate the pulley. The cable is wound around the winding drum by rotating the pulley to rotate the winding drum. Tension is applied to the cable by unwinding the wire to rotate the pulley and the winding drum in this way, and the loosening of the cable is suppressed by the application of the tension.

SUMMARY

However, in a case in which there is a difference between the diameter of the cable (electric wire) and the diameter of the wire, the winding perimeters of the winding drum and the pulley change depending on the amount of winding. The winding perimeter indicates the amount of winding of the cable or the wire in the unit amount of rotation of each of the winding drum and the pulley and is, for example, the length of the cable that can be wound in a case in which the winding drum makes one rotation. In a case in which the diameter of the cable is large and the cable is wound in double or triple layers, the diameter of the winding drum becomes large. Therefore, the winding perimeter also becomes large. In addition, in a case in which there is a difference between the diameter of the cable and the diameter of the wire and the amount of winding increases due to lap winding, a difference between the amount of change in the winding perimeter of the cable on the winding drum and the amount of change in the winding perimeter of the wire on the pulley increases.

In a case in which there is a difference between the winding perimeter of the cable on the winding drum and the winding perimeter of the wire on the pulley, the following problems occur. For example, as a first case, the following is considered: in a case in which the winding perimeter of the cable on the winding drum is larger than the winding perimeter of the wire on the pulley, the arm is rotated in a direction in which the cable is wound around the drum, that is, in a direction in which the first end portion connected to the cable approaches the support portion.

In the first case, the amount of unwinding of the wire from the pulley having one end fixed to the second end portion is determined according to the amount of orbital rotation of the arm, and the pulley and the winding drum are rotated in the same direction by the same amount according to the amount of unwinding. Then, since the winding perimeter of the winding drum is larger than that of the pulley, the cable is wound on the winding drum by an amount equal to or more than the amount of unwinding, and tension more than necessary which exceeds the tension required for winding is applied to the cable. In a case in which tension more than necessary is applied to the cable, there is a concern that the cable will be broken, which is not preferable.

Further, as a second case, the following is considered: the arm is orbitally rotated in a direction in which the cable is unwound from the winding drum, contrary to the first case. In the second case, the amounts of rotation of the winding drum and the pulley are determined according to the amount of unwinding of the cable from the winding drum. Since the winding perimeter of the pulley is smaller than the winding perimeter of the winding drum, the amount of winding of the wire is insufficient with respect to the amount of unwinding of the cable. Therefore, in the second case, the wire is loosened.

As described above, the following problem occurs: tension more than necessary is applied to the cable or a tension member that applies tension to the cable is loosened due to the difference between the winding perimeter of the cable and the winding perimeter of the tension member.

Here, the X-ray apparatus disclosed in JP1996-229027A (JP-H08-229027A) is configured such that a conical pulley whose diameter changes along the direction of the rotation shaft is used as the pulley and a wire guide groove through which the wire is guided is spirally formed in a conical surface of the pulley to prevent the occurrence of the difference between the winding perimeter of the cable (electric wire) wound over and over and the winding perimeter of the wire (see paragraph 0022 and FIG. 12 in JP1996-229027A (JP-H08-229027A)). However, in a case in which the conical pulley having the spiral wire guide groove formed therein is manufactured, processing is complicated and costly. Therefore, it has been required to more easily solve the problems caused by the difference between the winding perimeter of the cable and the winding perimeter of the tension member.

The technology according to the present disclosure provides a radiography apparatus that can more easily solve problems caused by a difference between a winding perimeter of a cable and a winding perimeter of a tension member.

According to a first aspect of the present disclosure, there is provided a radiography apparatus comprising: an arm that has a first end portion and a second end portion, one of which an irradiation unit that emits radiation is provided in and the other of which an image receiving unit that receives the radiation emitted from the irradiation unit and transmitted through a subject is attachable to, has an arc shape in a side view, and is orbitally rotatable around the subject in a posture in which the irradiation unit and the image receiving unit face each other; a support portion that has a track portion fitted to an outer peripheral portion of the arc shape of the arm and supports the arm to be orbitally rotatable; a cable that has one end electrically connected to at least one of the irradiation unit or the image receiving unit and is provided along an outer periphery of the arm from the first end portion of the arm to the support portion; a tension member that is used to apply tension to the cable in a case in which the arm is orbitally rotated in a first direction in which the first end portion approaches the support portion, has one end fixed to the second end portion of the arm, and is provided along the outer periphery of the arm from the second end portion to the support portion; a first reel that is rotated in a direction in which the cable is wound in a case in which the arm is orbitally rotated in the first direction and is rotated in a direction in which the cable is unwound in a case in which the arm is orbitally rotated in a second direction in which the second end portion approaches the support portion; a second reel that is rotated in a direction in which the tension member is unwound in a case in which the arm is orbitally rotated in the first direction, is rotated in a direction in which the tension member is wound in a case in which the arm is orbitally rotated in the second direction, and is provided to be independently rotatable with respect to the first reel; and a rotational force transmission member that, in a case in which one of the first reel and the second reel is rotated, transmits a rotational force in the same direction to the other, biases the first reel in a winding direction of the cable, biases the second reel in a winding direction of the tension member, and allows occurrence of a difference between an amount of rotation of the first reel and an amount of rotation of the second reel within a preset range in the transmission of the rotational force.

According to the above configuration, the cable that is provided along the outer periphery of the arm from the first end portion of the arm is wound around the first reel. Further, the tension member that is provided along the outer periphery of the arm from the second end portion of the arm is wound around the second reel. Therefore, in a case in which the arm is orbitally rotated, one of the cable and the tension member is wound and the other is unwound.

Here, the first reel and the second reel can be rotated independently of each other. In a case in which one of the first reel and the second reel is rotated, the rotational force in the same direction is transmitted to the other by the rotational force transmission member. The rotational force transmission member biases the first reel in the winding direction of the cable and biases the second reel in the winding direction of the tension member (the side opposite to the winding direction of the cable on the first reel). Further, the rotational force transmission member allows the occurrence of the difference between the amount of rotation of the first reel and the amount of rotation of the second reel within the preset range in a case in which the rotational force is transmitted.

Therefore, in a case in which the arm is orbitally rotated in the first direction, the second end portion is separated from the support portion. Therefore, the tension member rotates the second reel in the unwinding direction. The rotational force is transmitted from the second reel to the first reel by the rotational force transmission member, and the first reel is rotated in the same direction as the second reel. Since the unwinding direction of the second reel is the same as the winding direction of the first reel, the first reel winds the cable. Therefore, the loosening of the cable between the first end portion and the support portion is suppressed.

In addition, the rotational force transmission member biases the first reel in the winding direction of the cable and biases the second reel in the winding direction of the tension member. Further, the rotational force transmission member allows the occurrence of the difference between the amount of rotation of the first reel and the amount of rotation of the second reel within the preset range in a case in which the rotational force is transmitted.

Therefore, even in a case in which the winding perimeter of the cable on the first reel and the winding perimeter of the tension member on the second reel change due to the difference between the diameter of the cable and the diameter of the tension member, it is possible to perform the unwinding of the tension member and the winding of the cable while adjusting the amount of rotation of the first reel and the amount of rotation of the second reel by the difference between the winding perimeters. Therefore, it is possible to prevent tension more than necessary from being applied to the tension member and the cable or the occurrence of loosening due to the difference between the winding perimeters.

In the related art, in order to solve these problems, complicated processing, such as manufacturing a conical pulley having a spiral wire (tension member) guide groove formed therein, is performed to prevent the occurrence of the difference between the winding perimeters. On the other hand, according to the technology of the present disclosure, it is not necessary to perform the complicated processing. Therefore, it is possible to more easily solve the problems caused by the difference between the winding perimeter of the cable and the winding perimeter of the tension member.

According to a second aspect of the present disclosure, in the radiography apparatus according to the first aspect, the first reel and the second reel may be disposed coaxially.

According to the above configuration, since the first reel and the second reel are disposed coaxially, the configuration is simpler than a configuration in which the first reel and the second reel are disposed on different axes, and it is possible to save space.

According to a third aspect of the present disclosure, in the radiography apparatus according to the first aspect or the second aspect, the first reel and the second reel may be provided in the support portion.

According to the above configuration, since the support portion is a connection portion between the arm and the main body portion, it functions as a cable relay portion between the arm and the main body portion. The provision of the first reel in the support portion makes it easy to provide the cable. In addition, since the support portion is a portion serving as a base point of the arm that is orbitally rotated, it is an optimal position for drawing the cable and the tension member provided in the outer peripheral portion of the arm from the viewpoint of suppressing the complexity of the configuration. The provision of the first reel and the second reel at this position makes it possible to suppress the complexity of the configuration.

According to a fourth aspect of the present disclosure, in the radiography apparatus according to any one of the first to third aspects, in a case in which a thickness of the cable is larger than a thickness of the tension member, a first radius of a winding portion of the first reel in a state in which the cable is not wound may be smaller than a second radius of a winding portion of the second reel in a state in which the tension member is not wound.

According to the above configuration, in a case in which the thickness of the cable is larger than the thickness of the tension member, the first radius of the winding portion of the first reel is smaller than the second radius of the winding portion of the second reel. Therefore, it is possible to suppress an increase in the difference between the winding perimeter of the cable and the winding perimeter of the tension member in a case in which the cable and the tension member are wound by the first reel and the second reel, respectively. In addition, the winding portion means a portion on which the cable or the tension member is wound in the first reel and the second reel.

According to a fifth aspect of the present disclosure, in the radiography apparatus according to the fourth aspect, the first radius may be smaller than the second radius, and a difference between the first radius and the second radius may be equal to a difference between the thickness of the cable and the thickness of the tension member.

According to the above configuration, the difference between the first radius of the first reel and the second radius of the second reel is equal to a difference between the height of the cable and the height of the tension member. Therefore, in a state in which the cable and the tension member are wound once around the first reel and the second reel, respectively, the winding perimeter of the cable and the winding perimeter of the tension member are equal to each other.

This configuration in which the winding perimeter of the first reel in a state in which the cable is wound once and the winding perimeter of the second reel in a state in which the tension member is wound once are equal to each other makes it possible to reduce the maximum value of the difference between the winding perimeter of the cable and the winding perimeter of the tension member in a case in which the cable is wound a plurality of times.

According to a sixth aspect of the present disclosure, in the radiography apparatus according to any one of the first to fifth aspects, the cable may include a first cable for applying a voltage to a radiation tube of the irradiation unit.

According to the above configuration, since a relatively high voltage is applied to the radiation tube, the thickness of the insulating coating of the cable for applying the voltage is large. Therefore, the diameter of the cable for applying the voltage tends to be large. On the other hand, since the tension member only needs to apply tension, it is possible to reduce the diameter of the tension member. As described above, in a case in which the cable is a cable for applying a voltage to the radiation tube, a change in the difference between the winding perimeters corresponding to the amount of winding of the first reel and the difference between the winding perimeters of the first reel and the second reel also tend to be large. Therefore, it is highly necessary to adopt the technology of the present disclosure.

According to a seventh aspect of the present disclosure, in the radiography apparatus according to the sixth aspect, the cable may include the first cable and a second cable that is connected to the image receiving unit. The first cable and the second cable may be provided as a bundled cable group in an outer peripheral portion of the arm between the first reel and the first end portion, and the cable group may be fixed in the first end portion. The first cable and the second cable may branch off on a side opposite to the first reel with respect to a position where the cable group is fixed, one of the first cable and the second cable may be connected to one of the irradiation unit and the image receiving unit which is provided in the first end portion, and the other cable may be provided inside the arm to extend to the second end portion and may be connected to the other of the irradiation unit and the image receiving unit which is provided in the second end portion.

According to the above configuration, the first cable and the second cable are provided as a bundled cable group in the outer peripheral portion of the arm between the first reel and the first end portion. Since the cables provided in the outer peripheral portion of the arm are concentrated on the first end portion side of the arm, the complexity of electrical wiring is suppressed, as compared to a case in which the cables are provided in each of the first end portion and the second end portion in the outer peripheral portion of the arm.

According to an eighth aspect of the present disclosure, in the radiography apparatus according to any one of the first to seventh aspects, the irradiation unit may be provided in the first end portion.

According to the above configuration, in a case in which the radiography apparatus is used for moving image capture (also referred to as fluoroscopy), the irradiation unit is often disposed below the subject, and the image receiving unit is often disposed above the subject. In many cases, a moving image is captured during surgery. In this case, it is not preferable that a portion of the arm in which the cable is provided is disposed above the subject. For example, the reason is that, in a case in which the cable is loosened above the subject, the loosening may interfere with the surgery.

Therefore, the irradiation unit, which is often disposed below the subject in the capture of a moving image, is provided in the first end portion of the arm. As a result, in a case in which a moving image is captured, the portion of the arm in which the cable is provided can be disposed below the subject.

According to a ninth aspect of the present disclosure, in the radiography apparatus according to any one of the first to eighth aspects, the other end of the tension member may be fixed to the second reel.

According to the above configuration, since the other end of the tension member is fixed to the second reel, the length of the tension member can be smaller than that in, for example, a configuration in which both ends of the tension member are fixed to one end and the other end of the arm through the second reel. Therefore, it is possible to prevent the configuration of the second reel from being complicated.

According to a tenth aspect of the present disclosure, in the radiography apparatus according to any one of the first to ninth aspects, the tension member may be a belt or a wire.

According to the above configuration, since the belt or the wire is used as the tension member, it is possible to reduce the diameter of the tension member, and tension can be applied to the cable by the tension member.

According to an eleventh aspect of the present disclosure, in the radiography apparatus according to any one of the first to tenth aspects, the rotational force transmission member may be a spring that connects the first reel and the second reel and is expanded and contracted in a case in which the first reel and the second reel are rotated in opposite directions.

According to the above configuration, since the spring is used as the rotational force transmission member, it is possible to bias the first reel and the second reel in the winding directions of the cable and the tension member, respectively, while transmitting the rotational force with a simple configuration.

According to a twelfth aspect of the present disclosure, in the radiography apparatus according to the eleventh aspect, the spring may have one end that is attached to a first pin provided on a side surface of the first reel and the other end that is attached to a second pin provided on a side surface of the second reel.

According to the above configuration, since the first pin and the second pin attached to both ends of the spring are provided on the side surface of the first reel and the side surface of the second reel, respectively, it is possible to attach the spring to the first reel and the second reel with a simple configuration.

According to the technology of the present disclosure, it is possible to more easily solve the problems caused by the difference between the winding perimeter of the cable and the winding perimeter of the tension member.

BRIEF DESCRIPTION OF THE DRAWINGS

Exemplary embodiments according to the technique of the present disclosure will be described in detail based on the following figures, wherein:

FIG. 4 is an overall side view illustrating a cable and a tension member of the radiography apparatus according to an example of the embodiment.

DETAILED DESCRIPTION

Figure 1:
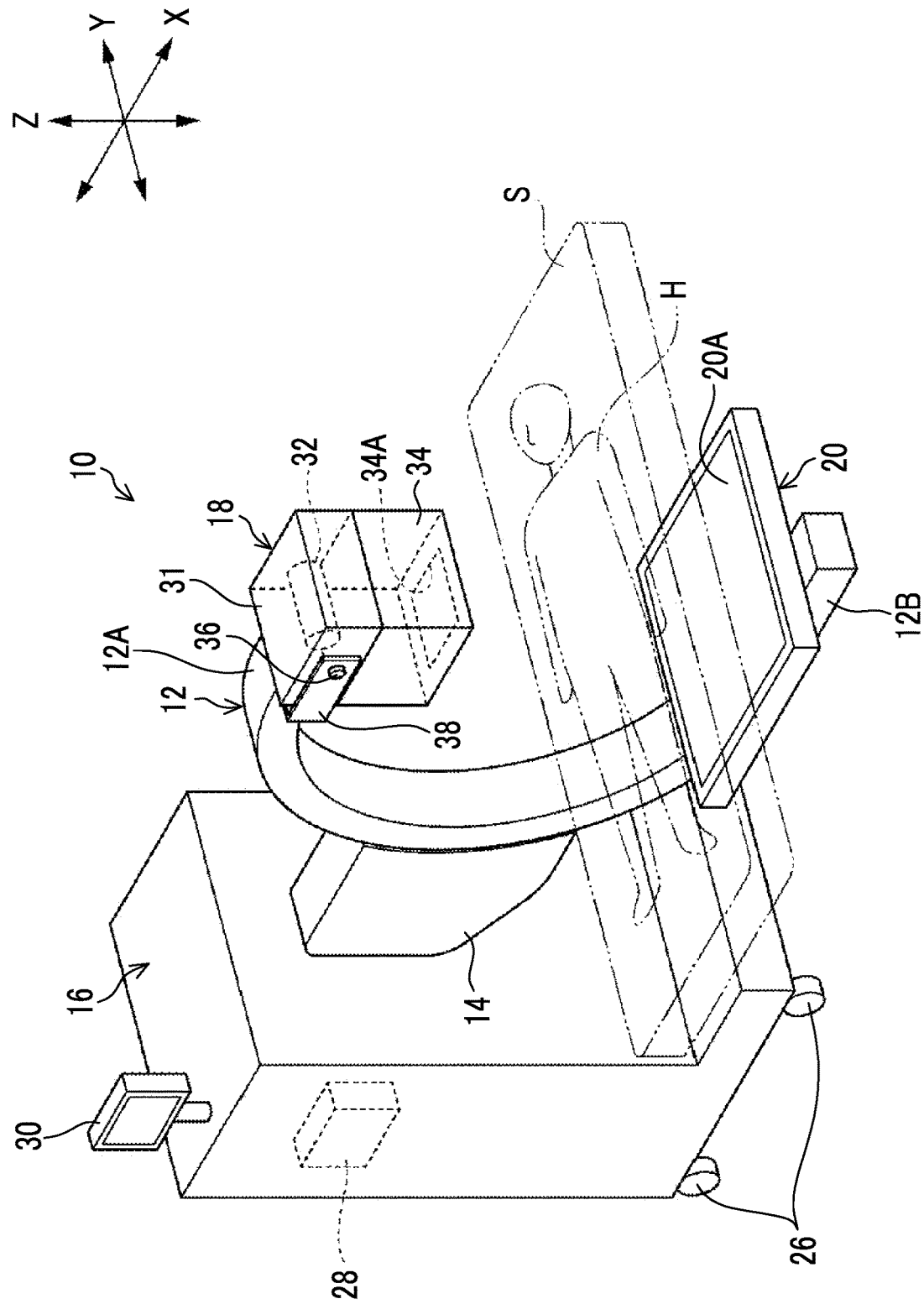
FIG. 1 is an overall perspective view illustrating a radiography apparatus according to an example of an embodiment.

Hereinafter, a radiography apparatus according to an example of an embodiment of the present disclosure will be described with reference to the drawings. In addition, in the drawings, an arrow X indicates a front-rear direction of the radiography apparatus, an arrow Y indicates a width direction of the radiography apparatus, and an arrow Z indicates a vertical direction.

(Overall Configuration of Radiography Apparatus)

A radiography apparatus 10 according to this embodiment illustrated in FIG. 1 is an apparatus that captures a radiographic image of a subject H. The radiography apparatus 10 can capture, for example, moving images and still images of the subject H. The capture of the moving image is performed, for example, in a case in which a treatment target part of the subject H is displayed as a moving image during surgery (also referred to as fluoroscopy or the like). In the capture of the moving image, for example, the moving image of the subject H is displayed on a monitor (not illustrated) that is provided separately from the radiography apparatus 10. Of course, data of the captured moving image may be stored in a memory of the radiography apparatus 10. In addition, in the case of the capture of the still image, the captured still image may be displayed on the monitor or may be stored in the memory of the radiography apparatus 10.

As illustrated in FIG. 1, the radiography apparatus 10 includes an arm 12 (referred to as a C-arm or the like) which has a C-shape (an arc shape) in a side view, a support portion 14 that supports the arm 12 such that the arm 12 can be orbitally rotated, and a main body portion 16 that supports the arm 12 to be axially rotatable. In addition, hereinafter, it is assumed that the side of the radiography apparatus 10 on which the arm 12 is provided is the front side of the radiography apparatus 10 and the side on which the main body portion 16 is provided is the rear side of the radiography apparatus 10.

(Configuration of Arm)

The arm 12 has two end portions of a first end portion 12A and a second end portion 12B. An irradiation unit 18 is provided in the first end portion 12A of the arm 12, and an image receiving unit 20 is provided in the second end portion 12B. The arm 12 can hold the irradiation unit 18 and the image receiving unit 20 in a posture in which they face each other. A space, into which the subject H and a bed S on which the subject H lies supine can be inserted, is ensured between the irradiation unit 18 and the image receiving unit 20. Further, in the following description, in some cases, in a side view of the arm 12 (as viewed from the Y direction in FIG. 1), a direction in which the irradiation unit 18 and the image receiving unit 20 are provided is referred to as the front side of the arm 12, and a side close to the support portion 14 is referred to as the rear side of the arm 12. The irradiation unit 18 is an example of an irradiator according to the present disclosure. The image receiving unit 20 is an example of an image receiver according to the present disclosure.

Figure 2A:
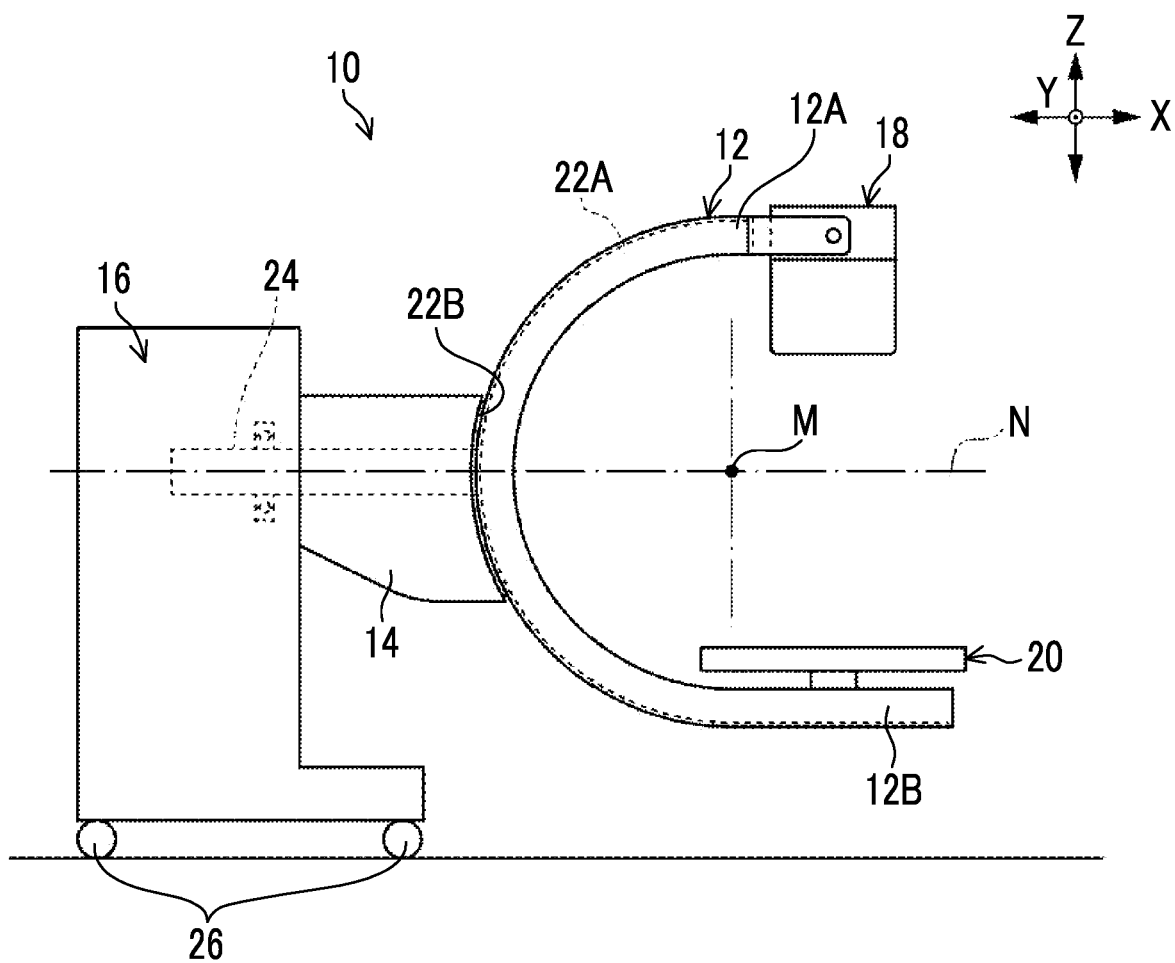
FIG. 2A is a side view illustrating the radiography apparatus according to an example of the embodiment.

As illustrated in FIG. 2A, the arm 12 is orbitally rotatable about an axis line M (an axis line parallel to the Y axis) with respect to a track portion 22B that is provided in the support portion 14. Further, the arm 12 is axially rotatable about an axis line N (an axis line parallel to the X axis) with respect to a bearing portion 23 that is provided in the main body portion 16.

Figure 5:
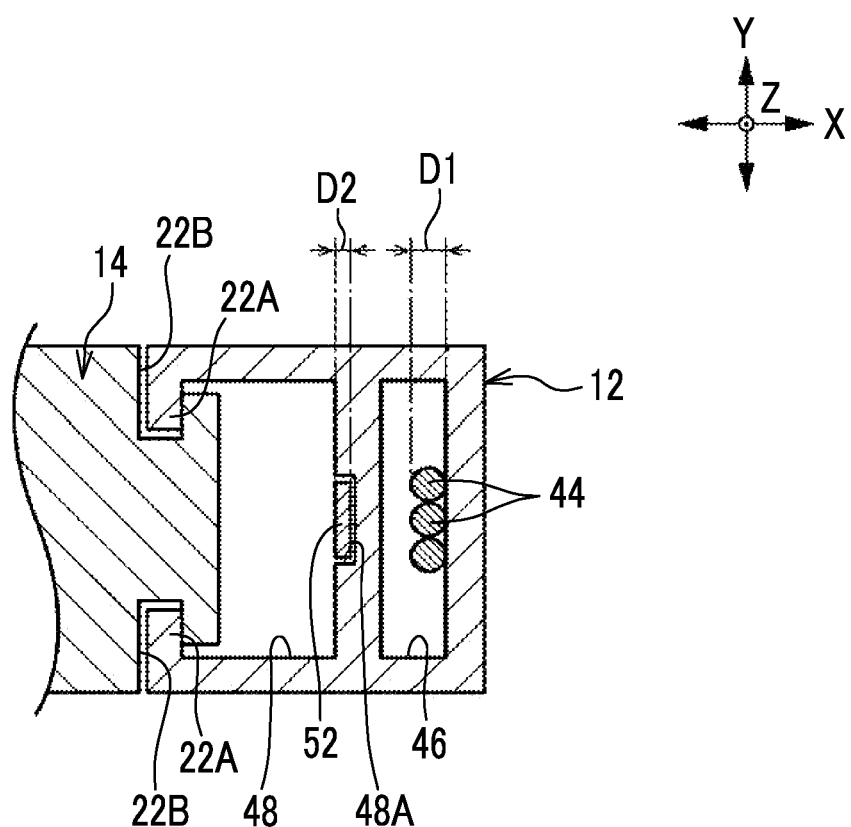
FIG. 5 is a cross-sectional view taken along the line A-A of FIG. 4.

Specifically, the track portion 22B has an arc shape that has the same radius as the arc of the arm 12. Moreover, a fitting portion 22A that is fitted to the track portion 22B is provided in an outer peripheral portion of the arm 12. The fitting portion 22A has an arc shape following the shape of the arm 12. As illustrated in FIG. 5, the track portion 22B has, for example, a groove shape, and the fitting portion 22A having a protruding shape is fitted to the track portion 22B. In addition, a roller (not illustrated) that assists the sliding of the fitting portion 22A with respect to the track portion 22B is interposed between the track portion 22B and the fitting portion 22A.

As illustrated in FIG. 2A, the fitting portion 22A formed in the arm 12 slides along the track portion 22B formed on the support portion 14. Therefore, the arm 12 can be orbitally rotated about the axis line M at the center of the arc of the arm 12 as a rotation center with respect to the support portion 14 and the main body portion 16.

Figure 2B:
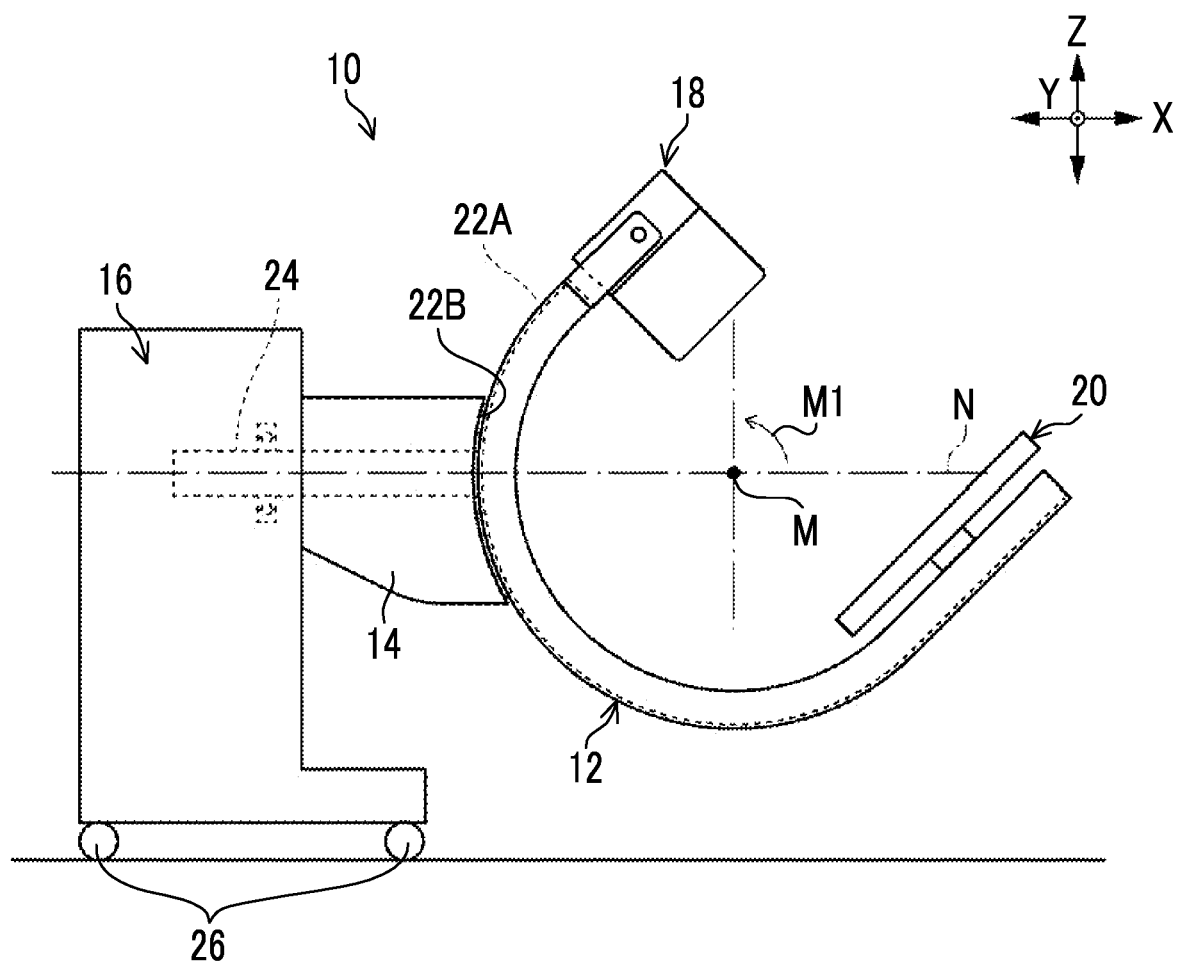
FIG. 2B is a side view illustrating a state in which an arm of the radiography apparatus illustrated in FIG. 2A is rotated in a direction of an arrow M1.
Figure 2C:
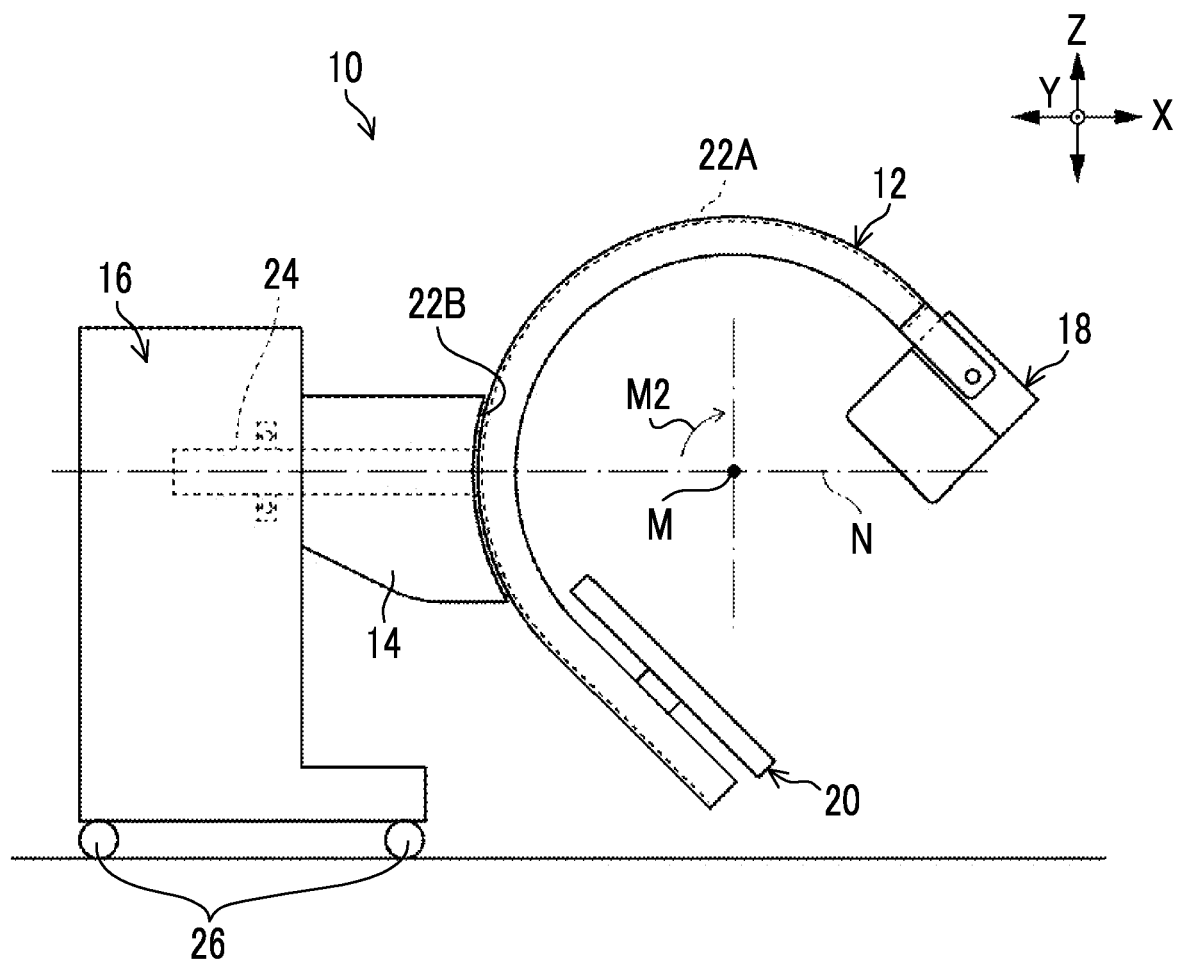
FIG. 2C is a side view illustrating a state in which the arm of the radiography apparatus illustrated in FIG. 2A is rotated in a direction of an arrow M2.

That is, as illustrated in FIGS. 2B and 2C, it is possible to orbitally rotate the arm 12 about the axis line M in the direction of an arrow M1 (counterclockwise in FIG. 2B) and the direction of an arrow M2 (clockwise in FIG. 2C). Therefore, the irradiation unit 18 and the image receiving unit 20 provided at both ends of the arm 12 can be rotated about the body axis (an axis parallel to the Y axis) of the subject H (see FIG. 1) in a posture in which they face each other.

Further, as illustrated in FIG. 2A, one end of a support shaft 24 that extends in a front-rear direction (X direction) of the radiography apparatus 10 is fixed to the arm 12. The other end of the support shaft 24 is supported by the main body portion 16 through the bearing portion 23. The support shaft 24 is rotated about the axis line N with respect to the bearing portion 23 such that the arm 12 and the support portion 14 are rotatable about the axis line N of the support shaft 24 as a rotation center with respect to the main body portion 16 as illustrated in FIGS. 3A to 3C.

Figure 3A:
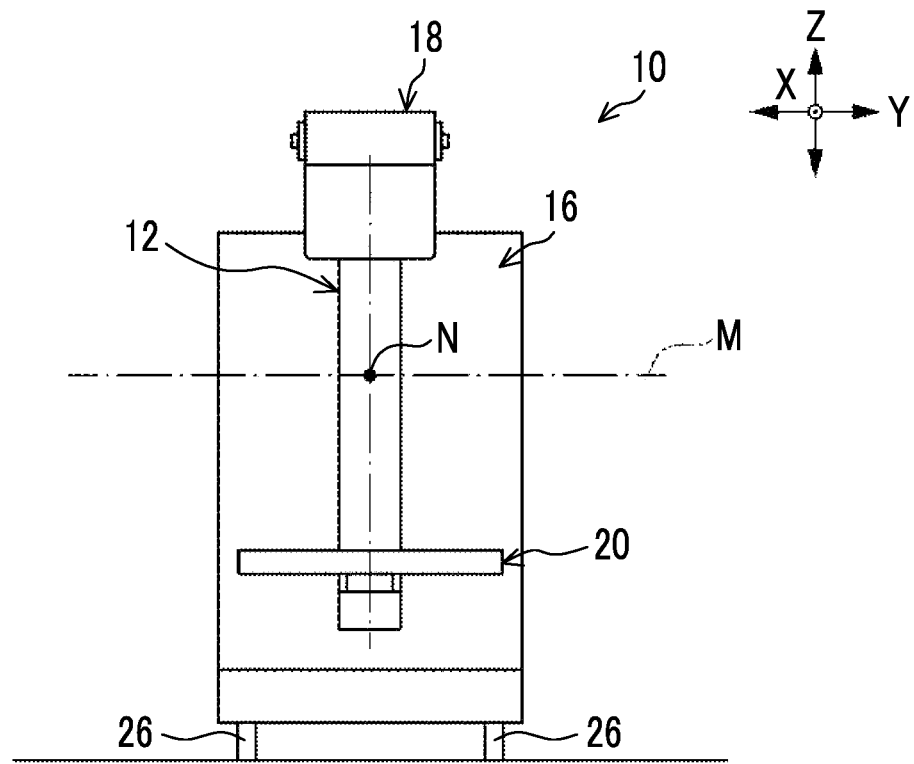
FIG. 3A is a front view illustrating the radiography apparatus according to an example of the embodiment.
Figure 3B:
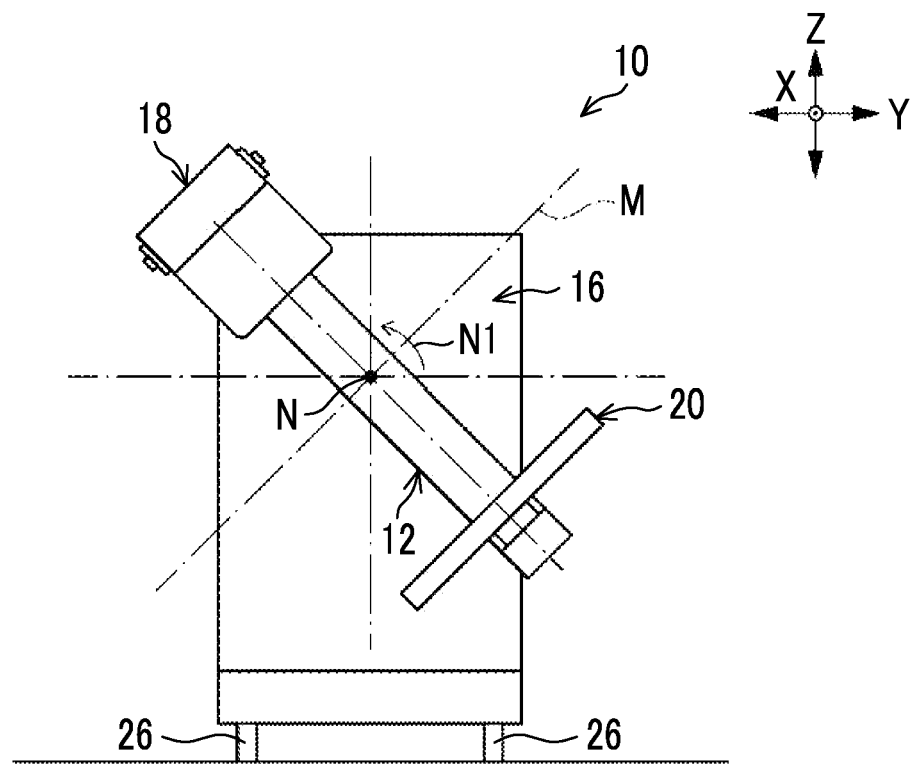
FIG. 3B is a front view illustrating a state in which the arm of the radiography apparatus illustrated in FIG. 3A is rotated in a direction of an arrow N1.
Figure 3C:
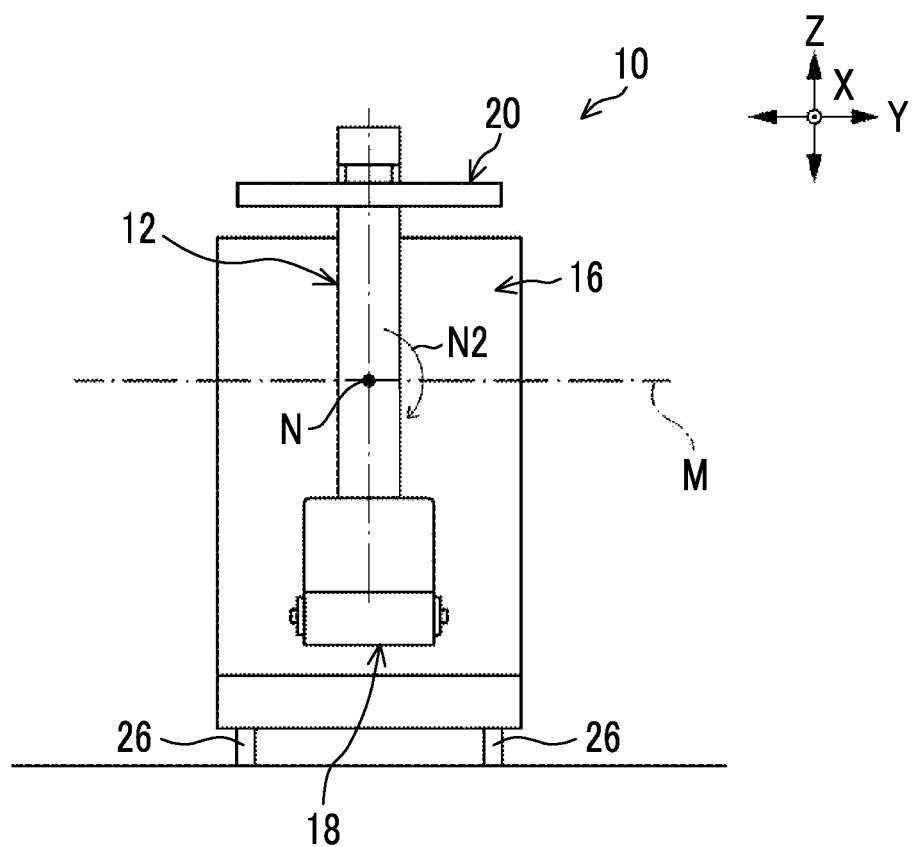
FIG. 3C is a front view illustrating a state in which the arm of the radiography apparatus illustrated in FIG. 3A is rotated 180° in a direction of an arrow N2.

That is, as illustrated in FIGS. 3B and 3C, it is possible to rotate the arm 12 about the axis line N in the direction of an arrow N1 (counterclockwise in FIG. 3B) and the direction of an arrow N2 (clockwise in FIG. 3C). Therefore, it is possible to reverse the positions of the irradiation unit 18 and the image receiving unit 20 provided at both ends of the arm 12 with respect to the subject H (see FIG. 1) in the vertical direction (Z-axis direction).

Here, in the posture of the arm 12 in which the irradiation unit 18 is disposed above the image receiving unit 20 as illustrated in FIG. 3A, a radiation tube 32 (see FIG. 1) included in the irradiation unit 18 is located above the subject H. Therefore, this posture is called, for example, an overtube posture. In addition, in the posture of the arm 12 in which the irradiation unit 18 is disposed below the image receiving unit 20 illustrated in FIG. 3C, the radiation tube 32 is located below the subject H. Therefore, this posture is called, for example, an undertube posture.

In the overtube posture, it is possible to increase a distance between the irradiation unit 18 and the subject H (see FIG. 1), as compared to the undertube posture. This makes it possible to image a relatively wide region in the overtube posture. Therefore, the overtube posture is mainly used to capture the still image of the subject H. On the other hand, in the undertube posture, the radiation emitted from the irradiation unit 18 is partially shielded by, for example, the bed S. Therefore, in the undertube posture, it is possible to reduce the amount of radiation exposure to, for example, a radiology technician or an operator (not illustrated) around the subject H (see FIG. 1). Therefore, the undertube posture is used for the capture of the moving image of the subject H in which radiation is continuously emitted.

(Configuration of Main Body Portion)

As illustrated in FIG. 1, a plurality of casters 26 are attached to a lower part of the main body portion 16 of the radiography apparatus 10, and the operator can push the radiography apparatus 10 by hand to move the radiography apparatus 10 into, for example, an operating room or a hospital ward. That is, the radiography apparatus 10 according to this embodiment is a mobile type.

Further, the main body portion 16 includes a control unit 28 that controls each unit of the radiography apparatus 10, such as the irradiation unit 18, and an operation panel 30 that is, for example, a touch panel type. In addition, the main body portion 16 comprises various switches (not illustrated) including, for example, a power switch of the radiography apparatus 10, a power circuit that supplies power to each unit of the radiography apparatus 10, a battery, and the like.

The operation panel 30 functions as an operation unit that inputs an operation instruction to each unit of the radiography apparatus 10 to operate each unit and a display unit that displays various kinds of information, such as a warning message and a radiographic image output from the image receiving unit 20.

(Configuration of Control Unit)

The control unit 28 transmits a control signal to the radiation tube 32 of the irradiation unit 18, which will be described below, to control, for example, the tube voltage, tube current, and irradiation time of radiation of the radiation tube 32. The control unit 28 controls the tube voltage to control the energy of the radiation. In addition, the control unit 28 controls the tube current and the irradiation time to control a radiation dose. In practice, since a high voltage is applied to the radiation tube 32, the control unit 28 controls the radiation tube 32 through a high-voltage generation device (not illustrated). In imaging, imaging conditions including, for example, the tube voltage, the tube current, and the irradiation time are set through the operation panel 30. The control unit 28 operates the irradiation unit 18 on the basis of the set imaging conditions.

The control unit 28 directs the irradiation unit 18 to perform moving image capture irradiation in which the irradiation unit 18 continuously emits radiation such that a moving image of the subject H can be captured. In a case in which a moving image is captured, the control unit 28 operates a detector of the image receiving unit 20 which will be described below in synchronization with the moving image capture irradiation by the irradiation unit 18. In a case in which a moving image is captured, basically, the irradiation time is not set as the imaging condition, and instructions to start and end the capture of the moving image are input through the operation panel 30. In a case in which the instruction to start the capture of a moving image is input, the control unit 28 directs the irradiation unit 18 to start the emission of radiation under preset imaging conditions.

In the capture of a moving image, the detector repeats an image detection operation at a preset frame rate while the moving image capture irradiation is performed. An image output by the detector is transmitted to the control unit 28. The control unit 28 sequentially outputs the received images to a monitor (not illustrated). Therefore, the moving image of the subject H is displayed on the monitor.

In addition, the control unit 28 directs the irradiation unit 18 to perform still image capture irradiation in which the irradiation unit 18 emits radiation for a shorter time than in the moving image capture irradiation such that a still image of the subject H can be captured.

In the capture of a still image, the control unit 28 operates the detector of the image receiving unit 20 in synchronization with the irradiation timing in the still image capture irradiation by the irradiation unit 18. For example, an instruction to capture a still image is input through an irradiation switch (not illustrated) that is connected to the control unit 28. In the capture of a still image, the irradiation time is, for example, in the order of several tens of milliseconds to several hundreds of milliseconds. In a case in which the instruction to capture a still image is input, the control unit 28 operates the irradiation unit 18 on the basis of preset imaging conditions. In the capture of a still image, in a case in which the set irradiation time elapses, the irradiation operation of the irradiation unit 18 ends since the irradiation time is set in the imaging conditions.

In a case in which the irradiation ends, the detector starts to output the detected image. The image output by the detector is transmitted to the control unit 28. The control unit 28 stores data of the still image in a memory (not illustrated). Then, the stored still image is displayed on the monitor (not illustrated). Therefore, the still image of the subject H is displayed on the monitor. Further, the still image may be displayed on the operation panel 30 in order to check the captured still image immediately after imaging.

(Configuration of Irradiation Unit)

The irradiation unit 18 comprises a radiation source 31 and an irradiation field limiter 34. The radiation source 31 comprises the radiation tube 32 that generates radiation. The radiation is, for example, X-rays. The radiation tube 32 generates radiation by colliding electrons generated from a cathode with a target (anode). The position where the electrons collide with the target is a focus where radiation is emitted.

In addition, the irradiation field limiter 34 is provided below the radiation source 31. The irradiation field limiter 34 (also referred to as a collimator or the like) has a rectangular irradiation opening 34A. The radiation generated by the radiation tube 32 is emitted to the subject H through the irradiation opening 34A. The irradiation field limiter 34 can adjust the opening area of the irradiation opening 34A. The irradiation field limiter 34 has, for example, four shielding plates (not illustrated) that shield radiation. In each of the four shielding plates, each side corresponds to each side of the irradiation opening 34A and defines the irradiation opening 34A. The position of the shielding plates is changed to adjust the opening area of the irradiation opening 34A, and the irradiation field of the radiation emitted from the irradiation unit 18 is changed.

Further, the irradiation unit 18 can be rotated about an axis line of a rotation shaft 36 that extends in the width direction (the Y direction in FIG. 1) of the radiography apparatus 10 as a rotation center with respect to the arm 12. Specifically, a pair of attachment plates 38 (only one attachment plate is illustrated in FIG. 1) are fixed to the first end portion 12A of the arm 12.

The pair of attachment plates 38 are disposed such that both sides of the irradiation unit 18 in the width direction are interposed therebetween and are connected to both side surfaces of the irradiation unit 18 in the width direction. The rotation shafts 36 are provided on each of the side surfaces of the irradiation unit 18 facing the attachment plates 38 so as to protrude. The rotation shafts 36 are supported by the pair of attachment plates 38 through bearings (not illustrated). Therefore, the irradiation unit 18 can be rotated about the axis line of the rotation shaft 36 as the rotation center with respect to the attachment plates 38, and the orientation of the irradiation opening 34A of the irradiation unit 18 can be changed in the front-rear direction of the arm 12. The orientation of the irradiation opening 34A can be changed to change the irradiation direction of radiation.

(Configuration of Image Receiving Unit)

As illustrated in FIG. 1, the image receiving unit 20 is provided in the second end portion 12B of the arm 12 which is a position facing the irradiation unit 18. In addition, in this embodiment, the image receiving unit 20 is fixed to the second end portion 12B of the arm 12 so as not to be detachable. However, the image receiving unit 20 may be attached to the second end portion 12B of the arm 12 so as to be detachable.

The image receiving unit 20 comprises the detector provided in a housing. The image receiving unit 20 has an image receiving surface 20A that receives the radiation which has been emitted from the irradiation unit 18 and then transmitted through the subject H. The radiation carrying the information of the subject H is incident on the image receiving surface 20A.

The detector is, for example, a flat panel detector (FPD) of a digital radiography (DR) type. The FPD has a detection surface in which a plurality of pixels are two-dimensionally arranged and a thin film transistor (TFT) panel (not illustrated) for driving the pixels. The radiation is incident on the detection surface of the detector through the image receiving surface 20A. The detector converts the incident radiation into an electric signal and outputs a radiographic image indicating the subject H on the basis of the converted electric signal. For example, the detector is an indirect conversion type that converts radiation into visible light using a scintillator and converts the converted visible light into an electric signal. In addition, the detector may be a direct conversion type that directly converts radiation into an electric signal. Further, the image receiving unit 20 may have any configuration other than the configuration using the FPD. For example, the image receiving unit 20 may have a configuration in which an image intensifier (I.I) and a camera are combined.

(Configuration of Cable)

As illustrated in FIG. 4, the irradiation unit 18 and the image receiving unit 20 are connected to, for example, the control unit 28 (see FIG. 1) and a power circuit (not illustrated) of the main body portion 16 by a cable 40 including a signal line for transmitting a control signal and a power line for supplying power.

Figure 6:
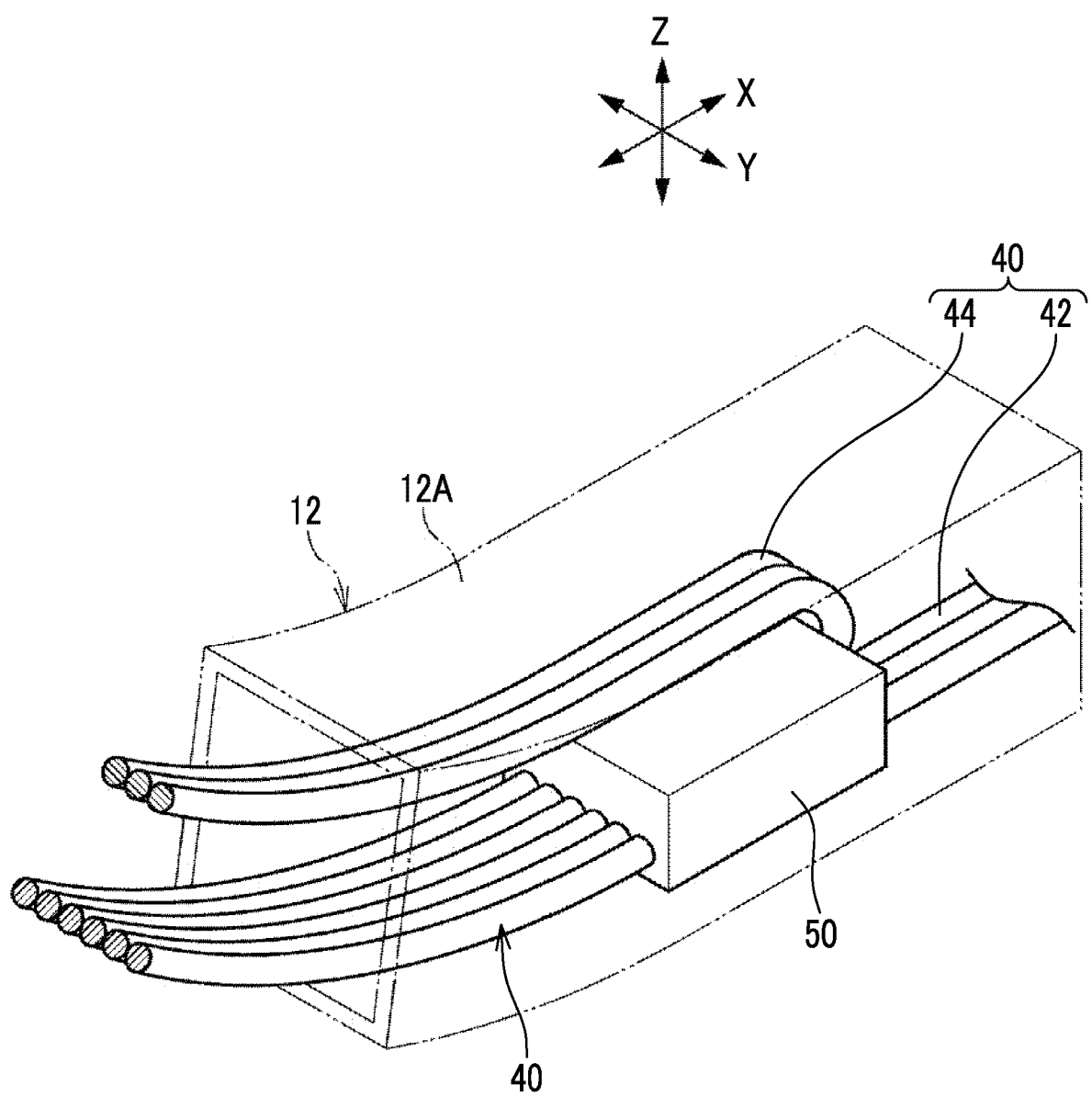
FIG. 6 is a partial perspective view illustrating a first end portion of the radiography apparatus according to an example of the embodiment.

As illustrated in FIGS. 5 and 6, the cable 40 comprises a plurality of (for example, three in this embodiment) first cables 42 and a plurality of (for example, three in this embodiment) second cables 44. The first cable 42 is for applying a voltage to the radiation tube 32 (see FIG. 1) of the irradiation unit 18 and has one end electrically connected to the irradiation unit 18 provided in the first end portion 12A of the arm 12 as illustrated in FIG. 4.

On the other hand, the second cable 44 supplies driving power to the image receiving unit 20 and relays various signals transmitted and received between the control unit 28 (see FIG. 1) and the detector in the image receiving unit 20. The various signals include, for example, a control signal transmitted from the control unit 28 to the detector and an image signal transmitted from the detector to the control unit 28. One end of the second cable 44 is electrically connected to the image receiving unit 20 provided in the second end portion 12B of the arm 12. Further, the second cable 44 is provided inside the arm 12 and extends to the first end portion 12A of the arm 12 along the arm 12.

As illustrated in FIG. 5, the arm 12 is a cylindrical body having a cavity therein and comprises a first hollow portion 46 that is provided on the inner peripheral side (front side) and a second hollow portion 48 that is provided on the outer peripheral side (rear side). The second cable 44 is provided in the first hollow portion 46 inside the arm 12.

Further, as illustrated in FIGS. 4 and 6, the first end portion 12A of the arm 12 is provided with a holding member 50 that holds one end of the cable 40 extending from the support portion 14. In the holding member 50, the cable 40 branches into the first cables 42 and the second cables 44. The first cable 42 extends to the irradiation unit 18 from the holding member 50 as a base point and is connected to the irradiation unit 18. On the other hand, the second cable 44 extends to the image receiving unit 20 and is connected to the image receiving unit 20.

In other words, the first cable 42 having one end connected to the irradiation unit 18 and the second cable 44 having one end connected to the image receiving unit 20 are fixed in the first end portion 12A of the arm 12 and are bundled into one cable group by the holding member 50. Then, one bundled cable group is provided as the cable 40 in the outer peripheral portion of the arm 12 and extends from the first end portion 12A to the support portion 14 along the outer periphery of the arm 12.

(Configuration of Belt)

Further, as illustrated in FIG. 4, one end of a belt 52 as a tension member is fixed to the second end portion 12B of the arm 12. The belt 52 is a member that is used to apply tension to the cable 40 and is provided from the second end portion 12B of the arm 12 to the support portion 14 along the outer periphery of the arm 12.

Specifically, as illustrated in FIG. 5, a groove 48A that extends along the arc of the arm 12 is formed in a front inner surface of the second hollow portion 48 of the arm 12, and the belt 52 extends along the arc of the arm 12 while being accommodated in the groove 48A. The belt 52 has a flat shape and is provided in a posture in which a longitudinal direction in a cross-sectional shape illustrated in FIG. 5 is aligned with the Y direction and a lateral direction (thickness direction) is aligned with the X direction. A thickness D2 of the belt 52 is smaller than a diameter (thickness) D1 of the cable 40.

(Configuration of Reel Unit)

Figure 7:
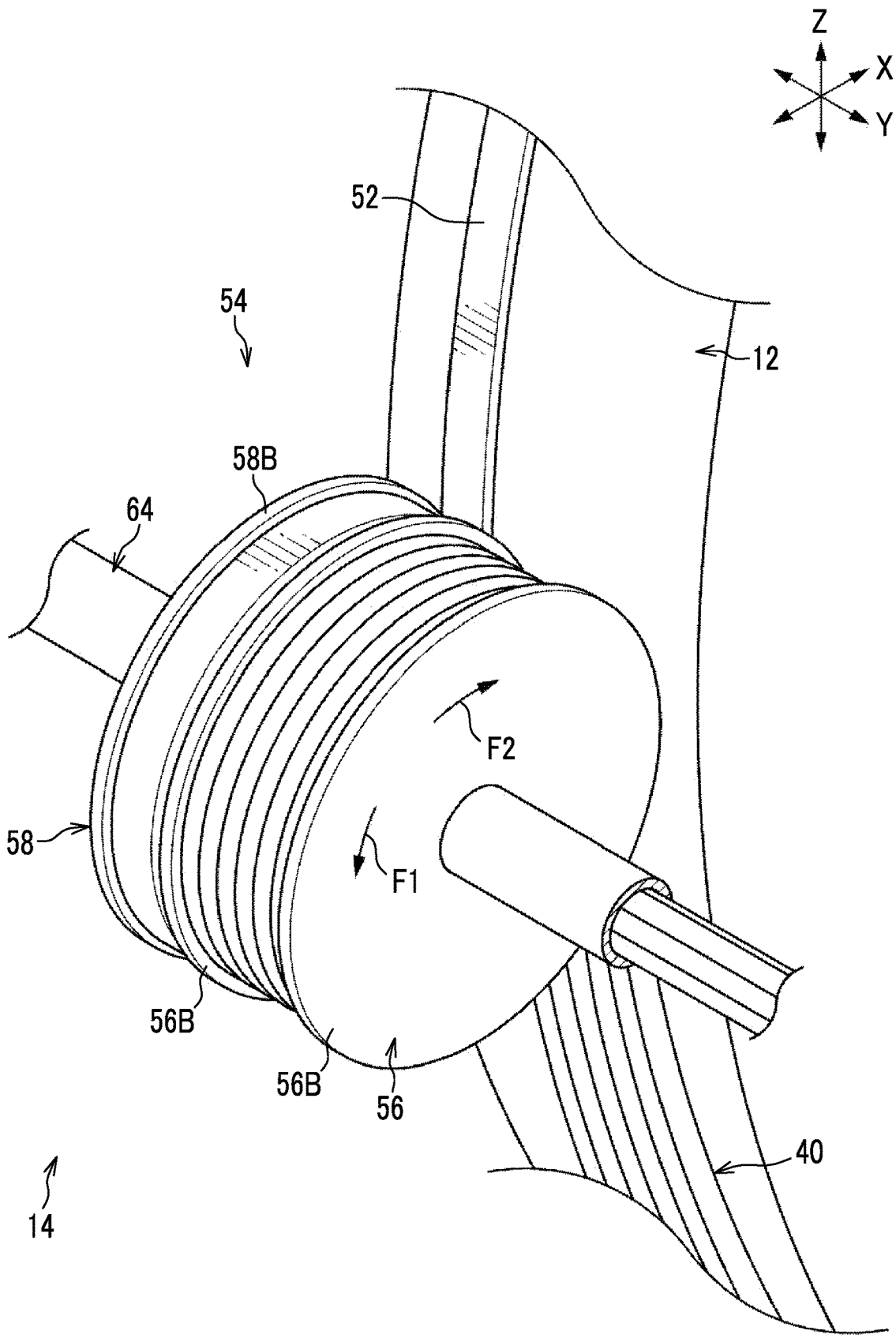
FIG. 7 is a partial perspective view illustrating a state in which the cable and the tension member of the radiography apparatus according to an example of the embodiment are wound around a first reel and a second reel, respectively.

As illustrated in FIG. 4, a reel unit 54 is provided in the support portion 14 of the radiography apparatus 10. The reel unit 54 winds and unwinds the cable 40 and the belt 52 as the arm 12 is orbitally rotated. As illustrated in FIG. 7, the reel unit 54 comprises a first reel 56 and a second reel 58 that is provided so as to be rotatable independently of the first reel 56.

Figure 8A:
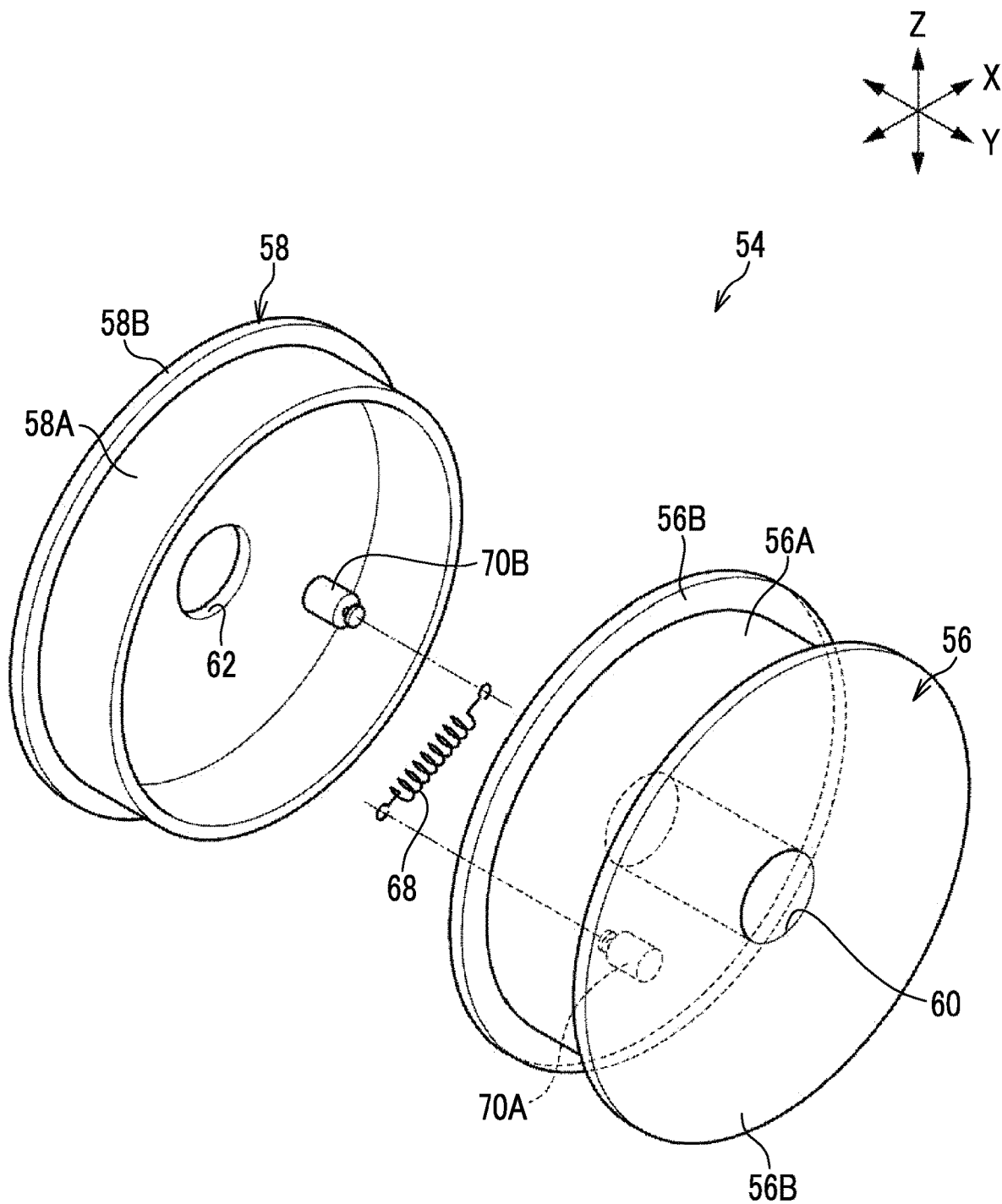
FIG. 8A is an exploded perspective view illustrating the first reel, the second reel, and a rotational force transmission member of the radiography apparatus according to an example of the embodiment.

As illustrated in FIG. 8A, the first reel 56 comprises a cylindrical winding portion 56A and a pair of flanges 56B that are provided on both end faces of the winding portion 56A. On the other hand, the second reel 58 comprises a cylindrical winding portion 58A and one flange 58B that is provided on one end surface of the winding portion 58A.

Figure 10:
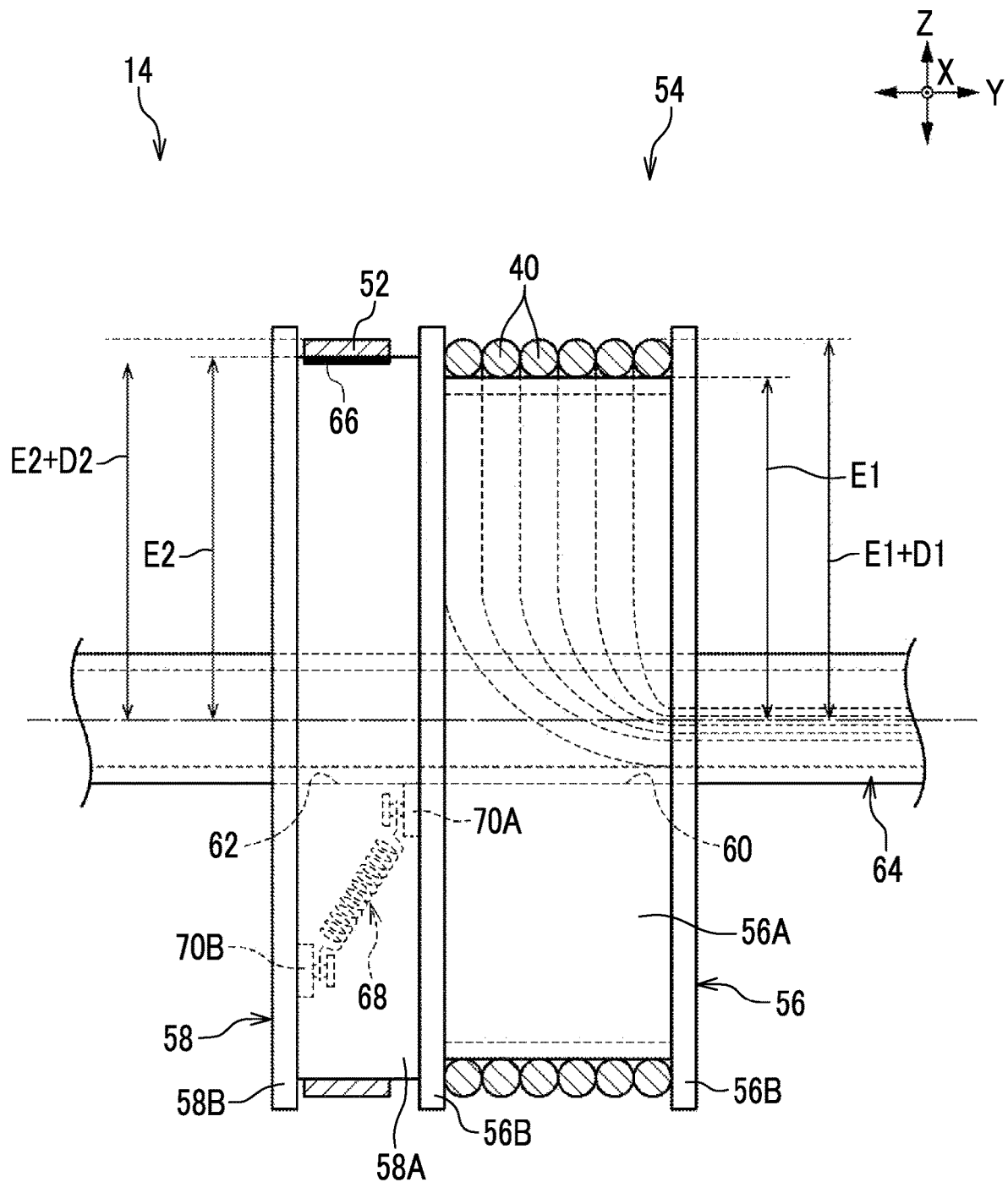
FIG. 10 is a cross-sectional view illustrating the first reel and the second reel of the radiography apparatus according to an example of the embodiment.

A shaft hole 60 is formed in the first reel 56, and a shaft hole 62 is formed in the second reel 58. As illustrated in FIG. 10, one rotation shaft 64 is inserted into each of the shaft hole 60 and the shaft hole 62 through a bearing portion (not illustrated). The rotation shaft 64 (see FIG. 7) has a cylindrical shape, and both end portions of the rotation shaft 64 in the axial direction are fixed to a frame (not illustrated) of the support portion 14. Therefore, the first reel 56 and the second reel 58 can be coaxially rotated independently about the axis line of the rotation shaft 64 as the center of rotation.

The cable 40 having one end fixed to the first end portion 12A (see FIG. 4) of the arm 12 extends to the support portion 14 and is wound around the winding portion 56A of the first reel 56 in the support portion 14. Further, as illustrated in FIG. 10, the other end of the cable 40 is drawn into the first reel 56, passes through the rotation shaft 64, extends to the main body portion 16 illustrated in FIGS. 1 and 4, and is connected to, for example, the control unit 28 (see FIG. 1) and the power circuit (not illustrated) of the main body portion 16.

On the other hand, the belt 52 having one end fixed to the second end portion 12B (see FIG. 4) of the arm 12 extends to the support portion 14 and is wound around the winding portion 58A of the second reel 58 in the support portion 14. Further, the other end of the belt 52 is fixed to an outer peripheral surface of the winding portion 58A of the second reel 58 by a fixing member 66 (see FIG. 10).

As illustrated in FIG. 8A, the first reel 56 and the second reel 58 are disposed side by side in the axial direction of the rotation shaft 64, and portions thereof which face each other in the axial direction come into contact with each other. Specifically, one flange 56B of the first reel 56 and the winding portion 58A of the second reel 58 come into contact with each other.

Figure 9A:
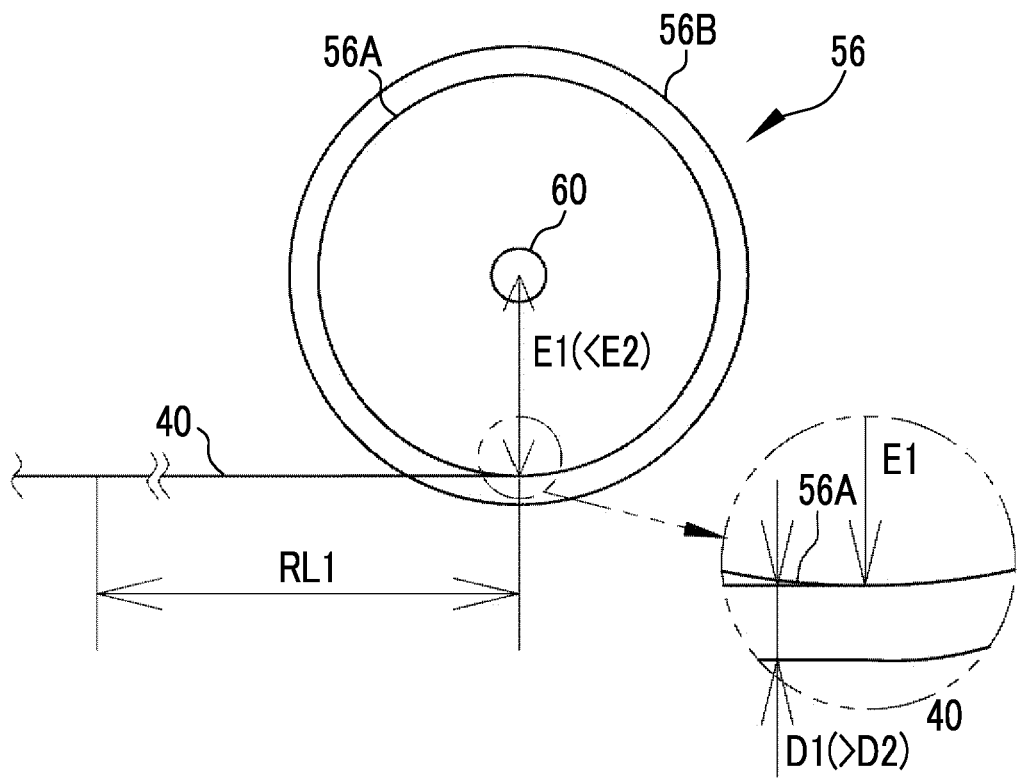
FIG. 9A is a diagram illustrating a perimeter difference between a winding perimeter of the first reel and a winding perimeter of the second reel and illustrates a first radius of the first reel and a diameter of the cable.
Figure 9B:
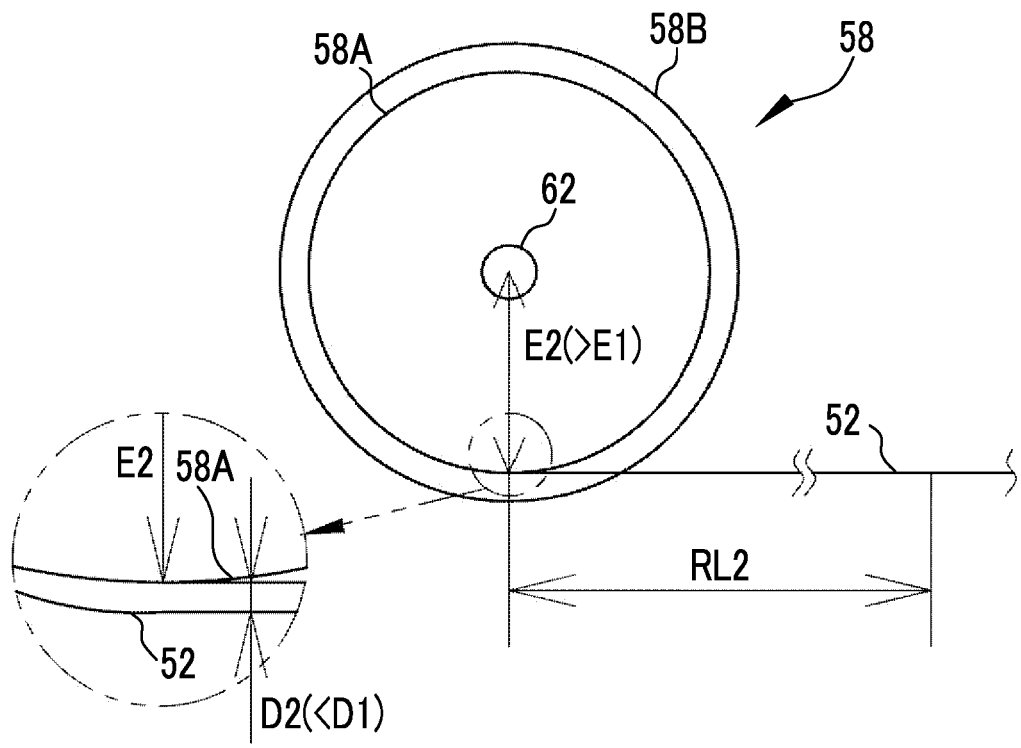
FIG. 9B is a diagram illustrating the perimeter difference between the winding perimeter of the first reel and the winding perimeter of the second reel and illustrates a second radius of the second reel and a thickness of the belt.

In addition, as illustrated in FIGS. 9A and 9B, in this embodiment, a first radius E1 of the winding portion 56A of the first reel 56 in a state in which the cable 40 is not wound is smaller than a second radius E2 of the winding portion 58A of the second reel 58 in a state in which the belt 52 is not wound. Further, a difference (E2−E1) between the first radius E1 and the second radius E2 is equal to a difference (D1−D2) between the diameter (thickness) D1 of the cable 40 and the thickness D2 of the belt 52.

That is, as illustrated in FIG. 10, the sum (E1+D1) of the first radius E1 of the winding portion 56A of the first reel 56 and the diameter D1 of the cable 40 is equal to the sum (E2+D2) of the second radius E2 of the winding portion 58A of the second reel 58 and the thickness D2 of the belt 52. Therefore, in a state in which the cable 40 and the belt 52 are wound once around the first reel 56 and the second reel 58, respectively, a winding perimeter of the cable 40 and a winding perimeter of the belt 52 are equal to each other.

Here, a winding perimeter RL indicates the amount of winding of the cable 40 and the belt 52 in the unit rotation amount of each of the first reel 56 and the second reel 58. The winding perimeter RL becomes larger as the amount of winding of the cable 40 and the belt 52 becomes larger.

For example, a winding perimeter RL1(1) of the cable 40 in the first turn of the first reel 56 is a circumference corresponding to the length of the first radius E1. Specifically, $RL1(1)=2\times E1\times \pi$ is established. Then, a winding perimeter RL1(2) of the cable 40 in the second turn is a circumference corresponding to the length obtained by adding the diameter D1 of the cable 40 to the first radius E1. Specifically, $RL1(2)=2\times(E1+D1)\times \pi$ is established. Then, a winding perimeter RL1(3) of the cable 40 in the third turn is a circumference corresponding to the length obtained by adding twice the diameter D1 to the first radius E1. Specifically, $RL1(3)=2\times(E1+2\times D1)\times \pi$ is established.

Similarly, a winding perimeter RL2(1) of the belt 52 in the first turn of the second reel 58 is a circumference corresponding to the length of the second radius E2. Specifically, $RL2(1)=2\times E2\times \pi$ is established. Then, a winding perimeter RL2(2) of the belt 52 in the second turn is a circumference corresponding to the length obtained by adding the thickness D2 of the belt 52 to the second radius E2. Specifically, $RL2(2)=2\times(E2+D2)\times \pi$ is established. Then, a winding perimeter RL2(3) of the belt 520 in the third turn is a circumference corresponding to the length obtained by adding twice the thickness D2 to the second radius E2. Specifically, $RL2(3)=2\times(E2+2\times D2)\times \pi$ is established.

As described above, the winding perimeter RL1 of the cable 40 on the first reel 56 and the winding perimeter RL2 of the belt 52 on the second reel 58 become larger as the amounts of winding of the cable 40 and the belt 52 become larger. Then, in a case in which there is a difference ΔD (ΔD=D1−D2) between the diameter D1 of the cable 40 and the thickness D2 of the belt 52, the rate of change in the winding perimeter RL1 and the winding perimeter RL2 also differs depending on the difference ΔD. Therefore, a perimeter difference ΔRL (ΔRL=RL1−RL2) between the winding perimeter RL1 and the winding perimeter RL2 occurs depending on the amounts of winding of the cable 40 and the belt 52.

In addition, in this example, the first radius E1 of the first reel 56 and the second radius E2 of the second reel 58 are different from each other. However, the difference between the first radius E1 and the second radius E2 is not the essential cause of the perimeter difference ΔRL which is a problem in the technology according to the present disclosure. The essential cause of the perimeter difference ΔRL which is a problem in the technology according to the present disclosure is that the diameter D1 of the cable 40 and the thickness D2 of the belt 52 are different from each other.

Therefore, the first radius E1 and the second radius E2 may be equal to each other. Even in this case, the perimeter difference ΔRL occurs.

(Configuration of Rotational Force Transmission Member)

Further, as illustrated in FIG. 8A, a spring 68 as a rotational force transmission member is provided between the first reel 56 and the second reel 58. The spring 68 is, for example, an extension spring. In one flange 56B of the first reel 56, a first pin 70A is provided on an outer surface which faces the second reel 58 so as to protrude. On the other hand, in the winding portion 58A of the second reel 58, a second pin 70B is provided on an inner surface of the flange 58B which faces the first reel 56 so as to protrude.

Figure 8B:
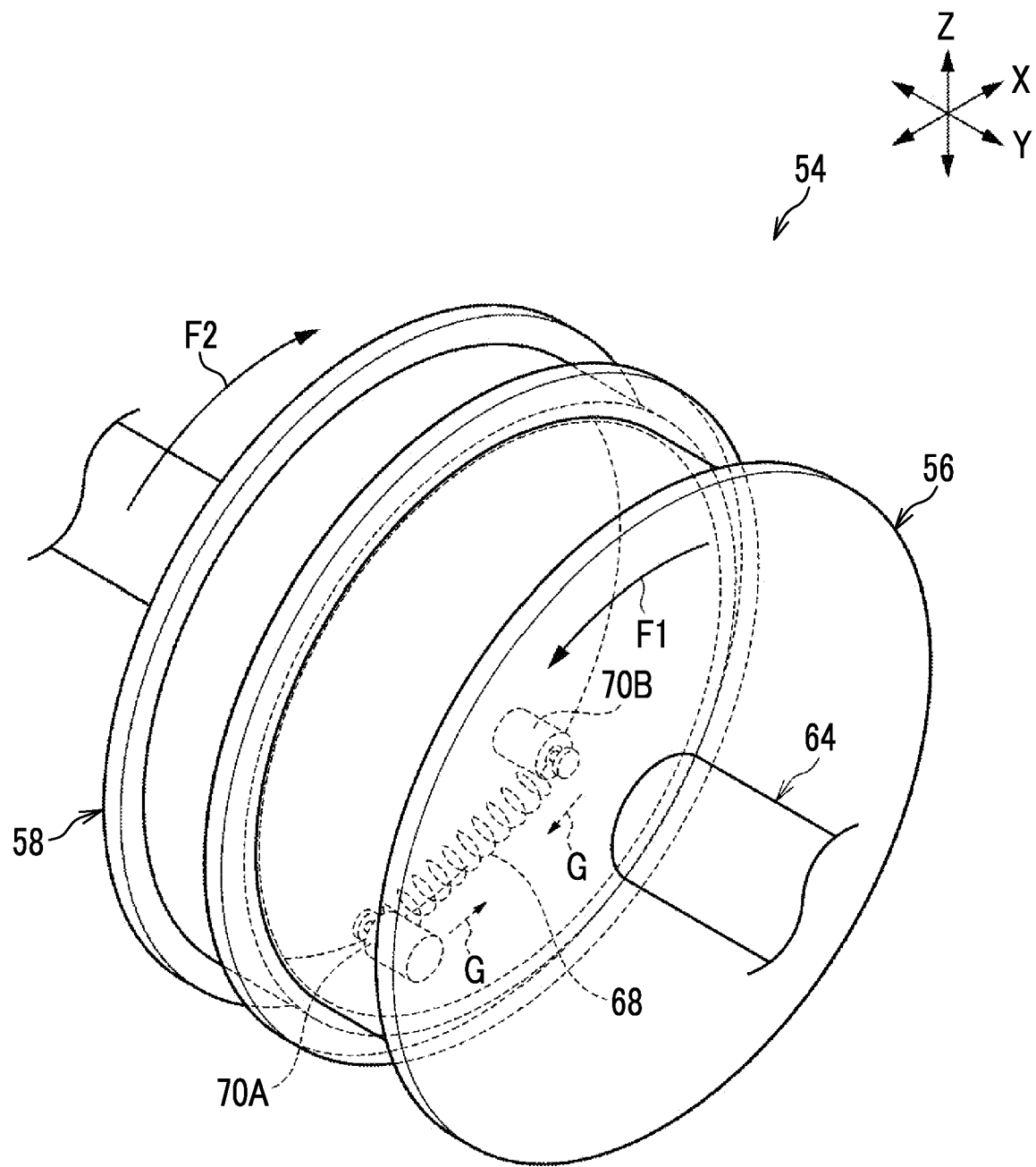
FIG. 8B is a perspective view illustrating a state in which the first reel, the second reel, and the rotational force transmission member illustrated in FIG. 8A are assembled.

As illustrated in FIG. 8B, one end of the spring 68 is fixed to the first pin 70A and the other end thereof is fixed to the second pin 70B such that the first reel 56 and the second reel 58 are connected by the spring 68. Further, the spring 68 is expanded and contracted in a case in which the first reel 56 and the second reel 58 are rotated in opposite directions.

In a case in which one of the first reel 56 and the second reel 58 is rotated by the spring 68, the rotational force in the same direction is transmitted to the other. Specifically, in a case in which the arm 12 is orbitally rotated in a first direction (the direction of the arrow M1 in FIG. 4) in which the first end portion 12A approaches the support portion 14, the second end portion 12B of the arm 12 is moved in a direction away from the support portion 14. In a case in which the second end portion 12B is moved in the direction away from the support portion 14, the belt 52 having one end fixed to the second end portion 12B is unwound from the second reel 58. Therefore, the second reel 58 around which the belt 52 is wound is rotated in the direction in which the belt 52 is unwound (in the direction of an arrow F1 illustrated in FIGS. 7 and 8B).

In this case, the rotational force of the second reel 58 is transmitted to the first reel 56 by the spring 68 (see FIG. 10), and the first reel 56 is rotated in the same direction (the direction of the arrow F1 illustrated in FIGS. 7 and 8B) as the second reel 58. The rotation in the direction of the arrow F1 is rotation in the direction in which the first reel 56 winds up the cable 40. Therefore, the cable 40 is wound around the first reel 56 by the rotation of the first reel 56 in the direction of the arrow F1. In a case in which the arm 12 is orbitally rotated in the first direction (the direction of the arrow M1 in FIG. 4) in which the first end portion 12A approaches the support portion 14, the cable 40 is loosened. Therefore, the loosening of the cable 40 is suppressed by the rotation of the first reel 56 in the direction of the arrow F1.

On the other hand, when the arm 12 is orbitally rotated in the second direction (the direction of the arrow M2 in FIG. 4) in which the second end portion 12B approaches the support portion 14, the first end portion 12A of the arm 12 is moved in the direction away from the support portion 14. In a case in which the second end portion 12B is moved in the direction approaching the support portion 14, the cable 40 having one end fixed to the first end portion 12A is unwound. Then, the first reel 56 around which the cable 40 is wound is rotated in the direction in which the cable 40 is unwound (the direction of the arrow F2 in FIGS. 7 and 8B).

In this case, the rotational force of the first reel 56 is transmitted to the second reel 58 by the spring 68 (see FIG. 10), and the second reel 58 is rotated in the same direction as the first reel 56 (the direction of the arrow F2 in FIGS. 7 and 8B). The rotation in the direction of the arrow F2 is rotation in the direction in which the second reel 58 winds up the belt 52. Therefore, the belt 52 is wound around the second reel 58 by the rotation of the second reel 58 in the direction of the arrow F2. In a case in which the arm 12 is orbitally rotated in the second direction (the direction of the arrow M2 in FIG. 4) in which the second end portion 12B approaches the support portion 14, the belt 52 is loosened. Therefore, the loosening of the belt 52 is suppressed by the rotation of the second reel 58 in the direction of the arrow F2.

Further, in this embodiment, the spring 68 is fixed to the first reel 56 and the second reel 58 in a state in which it is expanded to a length preset with respect to the natural length. That is, in the state in which the spring 68 is fixed to the first reel 56 and the second reel 58, biasing force is generated in the spring 68 in a direction in which the spring 68 is contracted (the direction of an arrow G in FIG. 8B) as illustrated in FIG. 8B.

The biasing force of the spring 68 biases the first reel 56 in the winding direction of the cable 40 (the direction of the arrow F1 in FIG. 8B) and biases the second reel 58 in the winding direction of the belt 52 (the direction of the arrow F2 in FIG. 8B).

Further, in a case in which the spring 68 transmits the rotational force of one of the first reel 56 and the second reel 58 to the other, it is allowed that the difference between the amount of rotation of one of the first reel 56 and the second reel 58 and the amount of rotation of the other occurs in a preset range, that is, a range in which the spring 68 can be expanded. Therefore, one of the first reel 56 and the second reel 58 can be rotated with respect to the other according to the biasing force of the spring 68 or against the biasing force of the spring 68.

(Operation and Effect)

Figure 11:
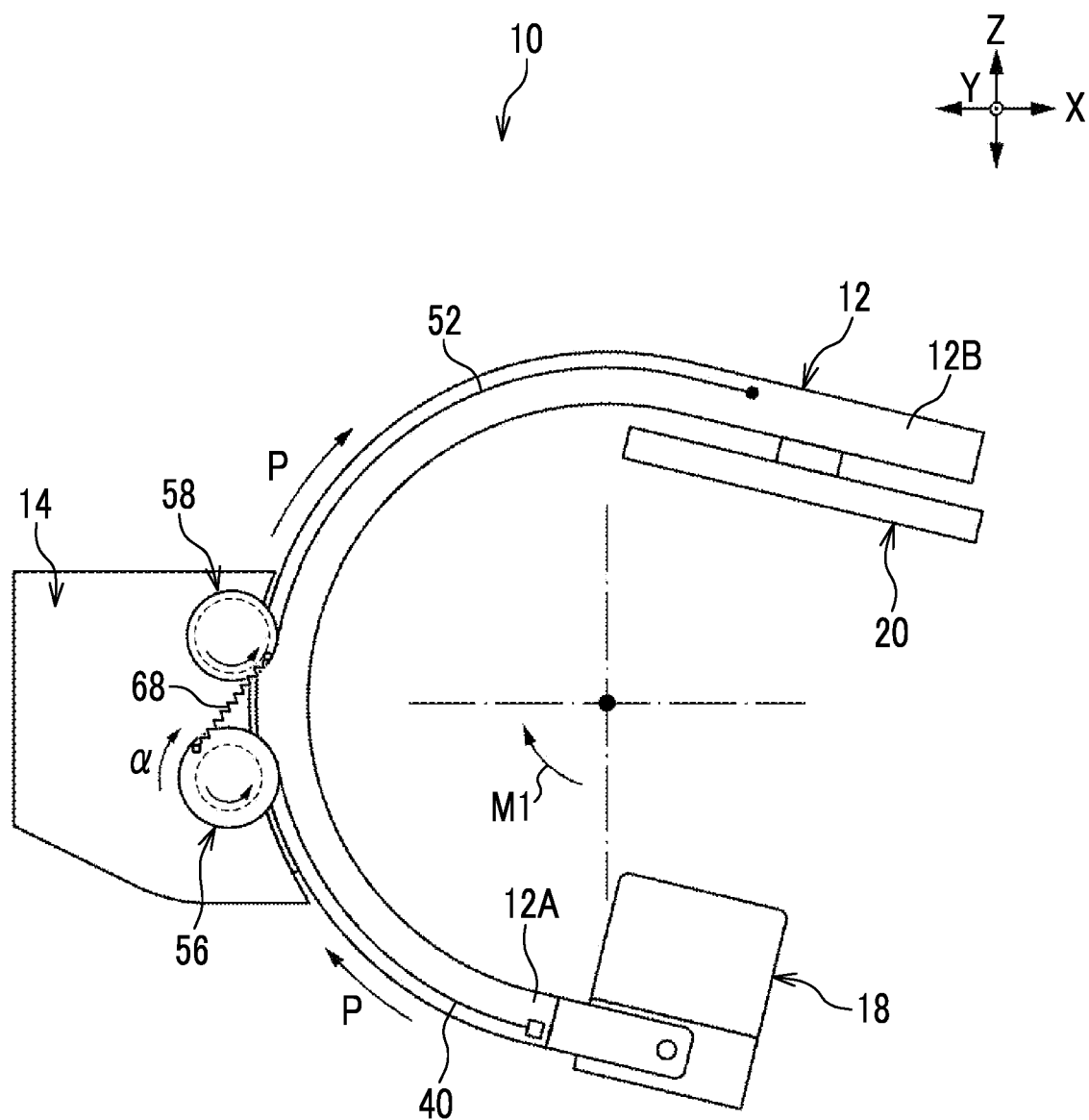
FIG. 11 is a side view schematically illustrating the first reel and the second reel in a case in which the arm of the radiography apparatus according to an example of the embodiment is orbitally rotated in a first direction.
Figure 12:
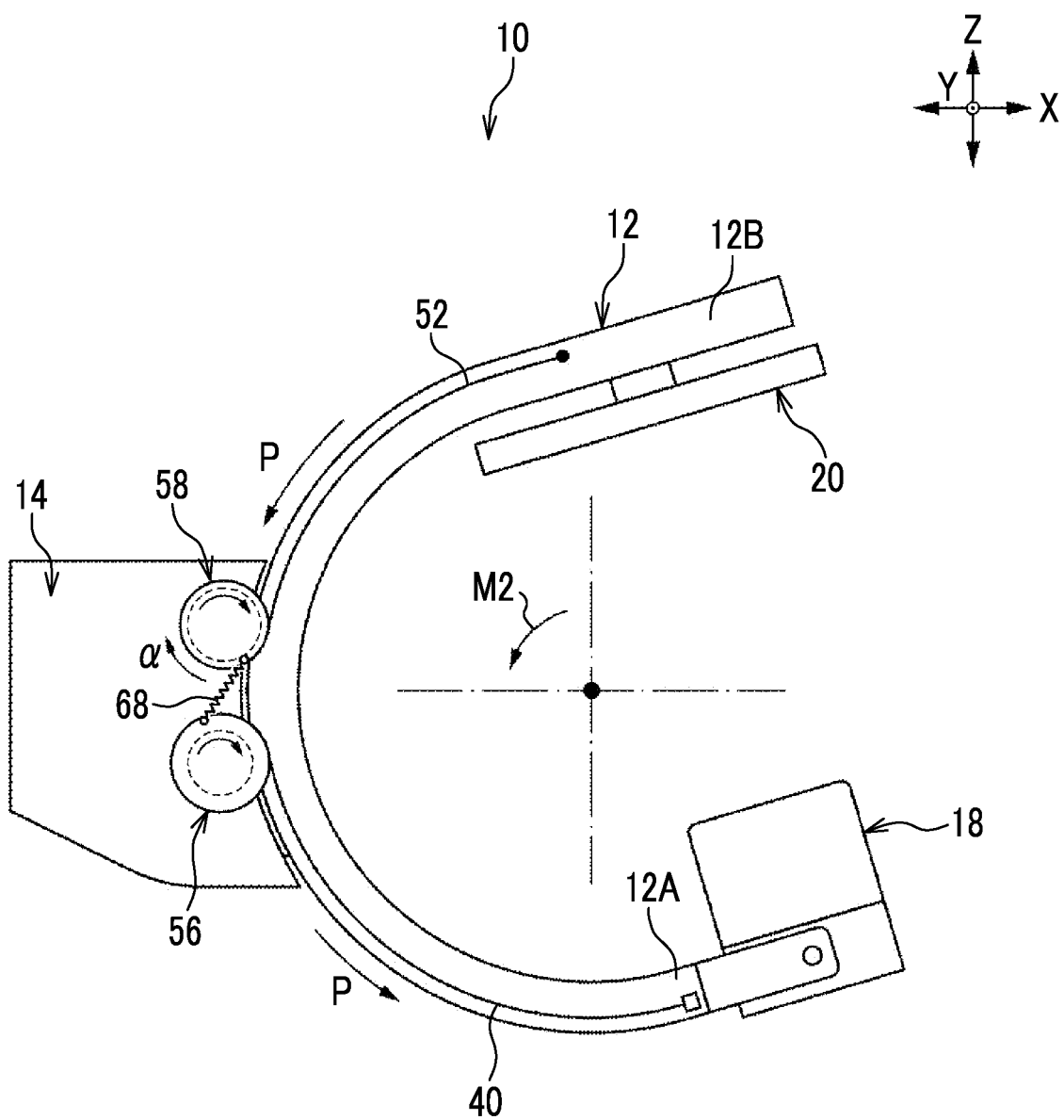
FIG. 12 is a side view schematically illustrating the first reel and the second reel in a case in which the arm of the radiography apparatus according to an example of the embodiment is orbitally rotated in a second direction.
Figure 13:
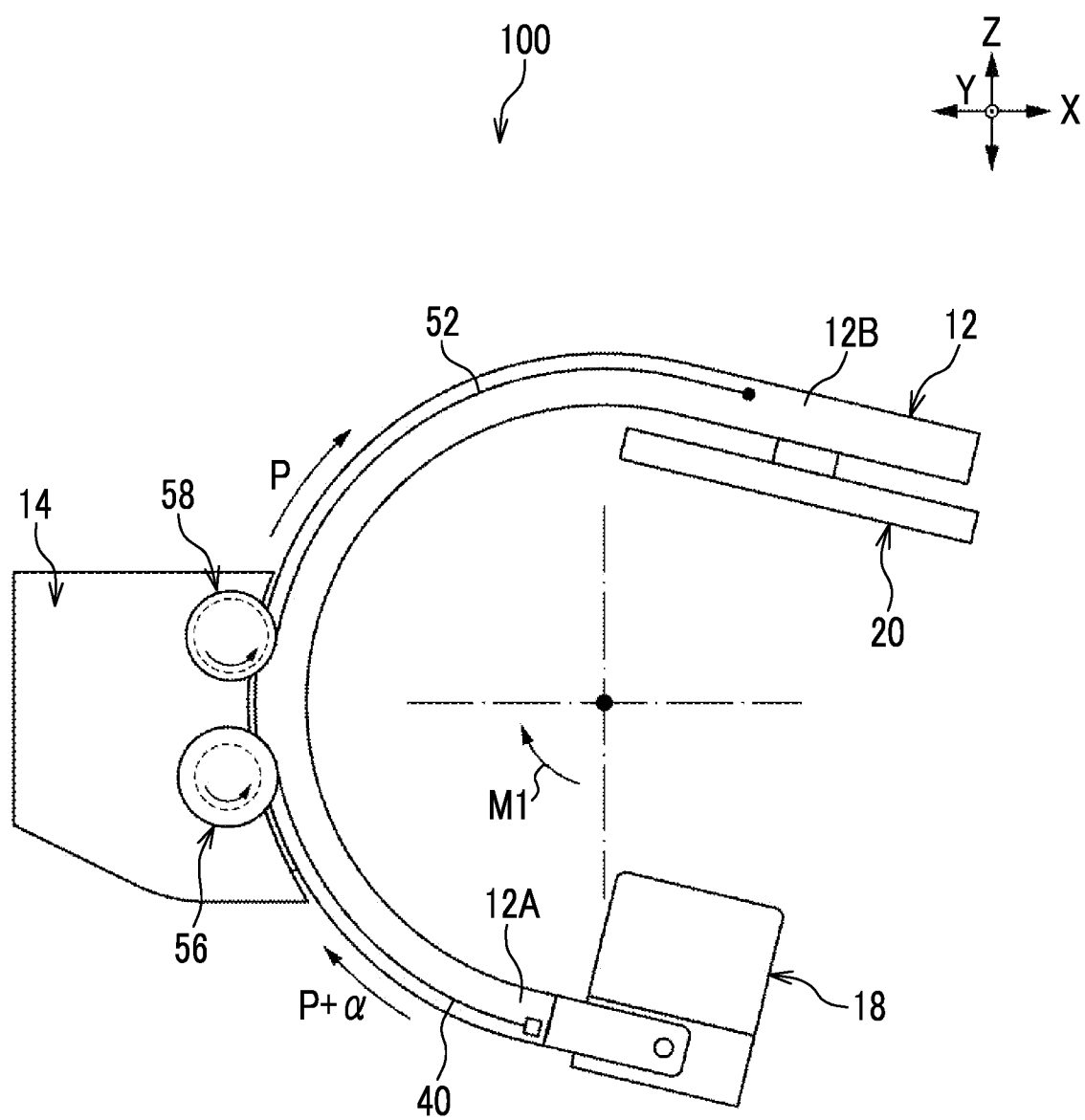
FIG. 13 is a side view schematically illustrating a first reel and a second reel in a case in which an arm of a radiography apparatus according to a comparative example is orbitally rotated in the first direction.
Figure 14:
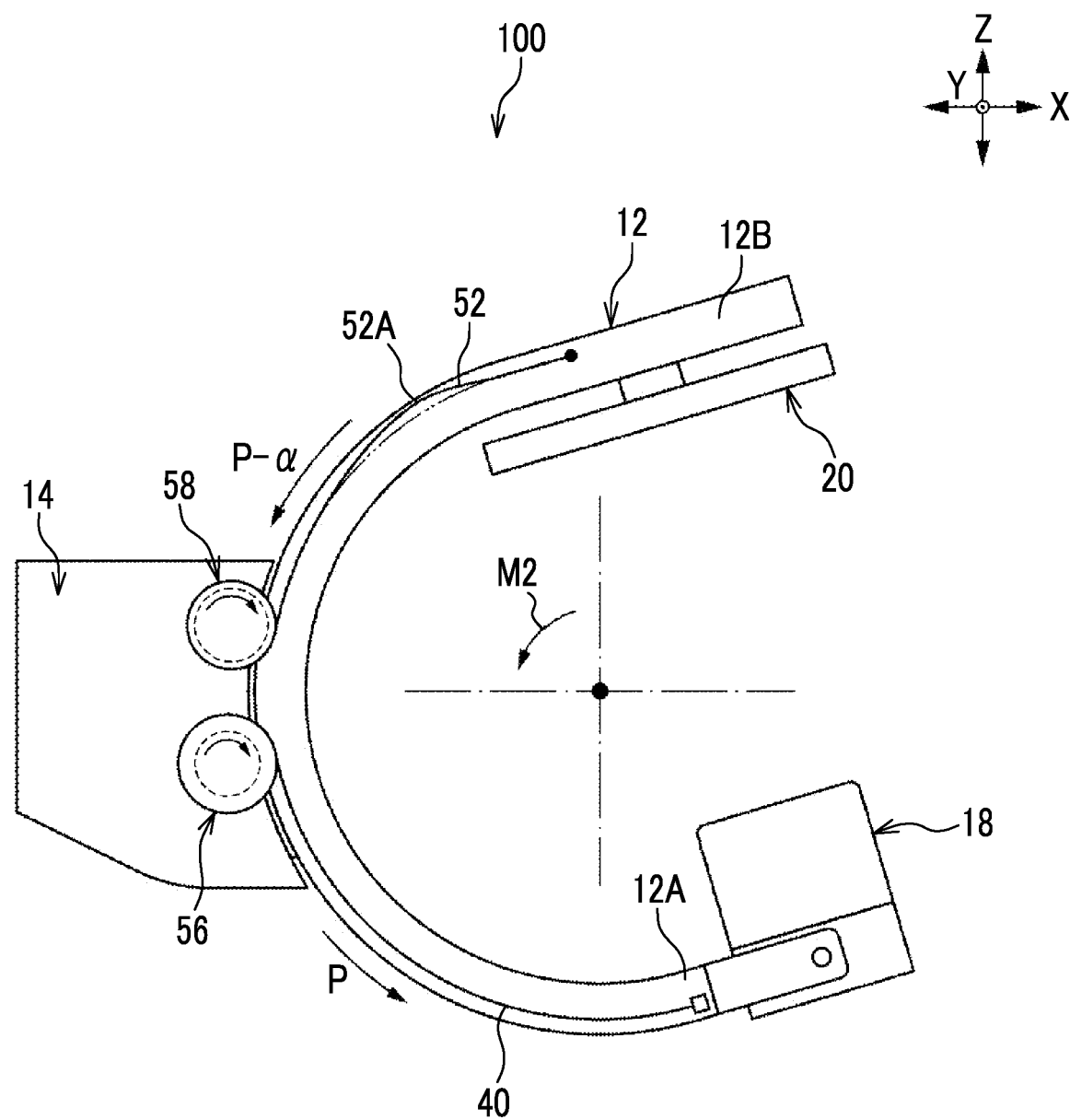
FIG. 14 is a side view schematically illustrating the first reel and the second reel in a case in which the arm of the radiography apparatus according to the comparative example is orbitally rotated in the second direction.

Next, the operation and effect of the radiography apparatus 10 according to this embodiment will be described with reference to FIGS. 11 to 14. FIGS. 11 and 12 illustrate the arm 12 and the support portion 14 of the radiography apparatus 10 according to this embodiment. On the other hand, FIGS. 13 and 14 illustrate an arm 120 and a support portion 140 of a radiography apparatus 100 according to a comparative example. The difference between the radiography apparatus 10 according to this embodiment and the radiography apparatus 100 according to the comparative example is that the comparative example does not have the spring 68 as the rotational force transmission member and the first reel 56 and the second reel 58 are integrated and always rotated in the same direction.

In addition, as illustrated in FIG. 7, the first reel 56 and the second reel 58 constituting the reel unit 54 are disposed at the position where they overlap each other in a side view (a direction seen from the Y direction) of the radiography apparatus 10. However, in FIGS. 11 to 14, for the sake of simplicity, the first reel 56 and the second reel 58 are illustrated side by side at positions that deviate from each other in the vertical direction (Z direction).

As illustrated in FIG. 11, in a case in which the arm 12 is orbitally rotated in the first direction (the direction of the arrow M1) in which the first end portion 12A of the arm 12 approaches the support portion 14, the cable 40 having one end fixed to the first end portion 12A also approaches the support portion 14 as the first end portion 12A is moved. In this case, it is necessary to wind the cable 40 with the first reel 56 provided in the support portion 14 to apply tension to the cable 40, in order to suppress the loosening of the cable 40.

The belt 52 is a member for applying tension to the cable 40, and one end thereof is fixed to the second end portion 12B of the arm 12. Therefore, in a case in which the arm 12 is orbitally rotated in the first direction (the direction of the arrow M1), the belt 52 is unwound from the second reel 58. The first reel 56 and the second reel 58 are held to be independently rotatable. However, in a case in which one of the first reel 56 and the second reel 58 is rotated, the rotational force in the same direction is transmitted to the other by the spring 68.

That is, in a case in which the arm 12 is orbitally rotated in the first direction (the direction of the arrow M1), the first end portion 12A of the arm 12 approaches the support portion 14, but the second end portion 12B of the arm 12 is conversely separated from the support portion 14. Therefore, the belt 52 having one end fixed to the second end portion 12B is unwound from the second reel 58, and the second reel 58 is rotated in the direction in which the belt 52 is unwound.

Further, the rotational force of the second reel 58 is transmitted to the first reel 56 by the spring 68 such that the first reel 56 is rotated in the same direction as the second reel 58. This rotation direction is the direction in which the belt 52 is unwound from the second reel 58 and the direction in which the cable 40 is wound around the first reel 56. Therefore, the cable 40 is wound around the first reel 56 even in a case in which the arm 12 is orbitally rotated in the first direction (the direction of the arrow M1). As a result, tension is applied to the cable 40, and the loosening of the cable 40 is suppressed.

Further, the spring 68 biases the first reel 56 in the winding direction of the cable 40 and biases the second reel 58 in the winding direction of the belt 52. In addition, the spring 68 allows the occurrence of the difference between the amount of rotation of the first reel 56 and the amount of rotation of the second reel 58 in a preset range in a case in which the rotational force is transmitted. Therefore, the following effects can be obtained.

That is, in a case in which there is a difference between the diameter D1 of the cable 40 and the thickness D2 of the belt 52, the perimeter difference ΔRL (ΔRL=RL1−RL2) between the winding perimeter RL1 of the cable 40 on the first reel 56 and the winding perimeter RL2 of the belt 52 on the second reel 58 occurs due to the thickness difference ΔD (ΔD=D1−D2) as illustrated in FIG. 9.

In a case in which the amount of winding of the cable 40 on the first reel 56 changes, the diameter of the first reel 56 changes. Therefore, the winding perimeter RL1 also changes. As described above, assuming that the winding perimeter of the cable 40 in the first turn on the first reel 56 is set as RL1(1), the winding perimeter RL1(2) of the cable 40 in the second turn is larger than the winding perimeter RL1(1). This is because the diameter of the first reel 56 including the second turn of the cable 40 is increased by a value corresponding to the diameter of the first turn of the cable 40. This holds for the second reel 58.

In a case in which the diameter D1 of the cable 40 and the thickness D2 of the belt 52 are equal to each other, the difference ΔD is zero. Therefore, even in a case in which the winding perimeters RL1 and RL2 of the first and second turns change in the first reel 56 and the second reel 58, respectively, the amounts of change in the winding perimeters RL1 and RL2 are the same. Therefore, in the first reel 56 and the second reel 58 that are rotated at the same timing, there is no perimeter difference ΔRL between the winding perimeter RL1 of the cable 40 on the first reel 56 and the winding perimeter RL2 of the belt 52 on the second reel 58.

However, in this embodiment, the diameter D1 of the cable 40 is larger than the thickness D2 of the belt. Since the belt 52 is for applying tension, the thickness D2 is small, and a change in the winding perimeter RL2 corresponding to the amount of rotation of the second reel 58 is negligible. On the other hand, since the cable 40 electrically connected to the irradiation unit 18 is a cable for applying a high voltage, the diameter D1 of the cable 40 is larger than that of a simple signal cable for control. Therefore, the change in the winding perimeter RL1 corresponding to the amount of rotation of the first reel 56 is not negligible, and the thickness difference ΔD from the belt 52 is also large.

Therefore, the change in the winding perimeter RL1 of the cable 40 on the first reel 56 and the winding perimeter RL2 of the belt 52 on the second reel 58 is so large that it is not negligible according to the change in the amount of winding of the first reel 56. In a case in which the perimeter difference ΔRL between the winding perimeters RL1 and RL2 of the first reel 56 and the second reel 58 occurs as described above, the following problems occur.

For example, in a case in which the winding perimeter RL1 of the cable 40 on the first reel 56 is larger than the winding perimeter RL2 of the belt 52 on the second reel 58, the following two cases of a first case and a second case are considered.

In the first case, as illustrated as a comparative example in FIG. 13, the arm 12 is orbitally rotated in the first direction (the direction of the arrow M1) such that the belt 52 is unwound from the second reel 58 and the cable 40 is wound around the first reel 56. In the first case, in a case in which the amount of rotation of the second reel 58 and the amount of rotation of the first reel 56 are completely equal to each other, the amount of winding of the cable 40 around the first reel 56 is larger than the amount of unwinding of the belt 52 from the second reel 58, and a tension more than necessary is applied to the cable 40.

That is, in a case in which the arm 12 is orbitally rotated in the first direction, the amount of unwinding P of the belt 52 from the second reel 58 is determined according to the amount of movement (represented by P) of the arm 12. The amount of rotation of the second reel 58 is determined according to the amount of unwinding P. The amount of rotation and the rotation direction of the first reel 56 are the same as those of the second reel 58.

Since the diameter D1 of the cable 40 is larger than the thickness D2 of the belt 52, the winding perimeter RL1 of the first reel 56 is larger than the winding perimeter RL2 of the second reel 58. Therefore, the amount of winding P+α of the cable 40 on the first reel 56 is larger than the amount of winding P of the belt 52 on the second reel 58. As a result, a tension equal to or more than the tension required to suppress loosening is applied to the cable 40. In a case in which the tension is too high, there is a concern that the cable 40 will be broken.

Further, in the second case, as illustrated as a comparative example in FIG. 14, the arm 12 is orbitally rotated in the second direction (the direction of the arrow M2) such that the cable 40 is unwound from the first reel 56 and the belt 52 is wound around the second reel 58. In the second case, in a case in which the amount of rotation of the second reel 58 and the amount of rotation of the first reel 56 are completely equal to each other, the amount of winding of the belt 52 on the second reel 58 is smaller than the amount of unwinding of the cable 40 from the first reel 56. Therefore, the belt 52 is loosened. Reference numeral 52A indicates a portion in which the belt 52 is loosened.

That is, in a case in which the arm 12 is orbitally rotated in the second direction, the amount of unwinding P of the cable 40 from the first reel 56 is determined according to the amount of movement (represented by P) of the arm 12. The amount of rotation of the first reel 56 is determined according to the amount of unwinding P. The amount of rotation and the rotation direction of the second reel 58 are also the same as those of the first reel 56.

Since the diameter D1 of the cable 40 is larger than the thickness D2 of the belt 52, the winding perimeter RL2 of the second reel 58 is smaller than the winding perimeter RL1 of the first reel 56. Therefore, the amount of winding P−α of the belt 52 on the second reel 58 is less than the amount of unwinding P of the cable 40 from the first reel 56. As a result, the belt 52 is loosened.

On the other hand, as illustrated in FIGS. 11 and 12, in the radiography apparatus 10 according to this embodiment, the first reel 56 and the second reel 58 are connected by the spring 68 as the rotational force transmission member. In a case in which one of the first reel 56 and the second reel 58 is rotated, the spring 68 not only transmits the rotational force in the same direction to the other, but also biases the first reel 56 in the winding direction of the cable 40 and the second reel 58 in the winding direction of the belt 52. Further, the spring 68 allows the occurrence of the difference between the amount of rotation of the first reel 56 and the amount of rotation of the second reel 58 within a preset range in a case in which the rotational force is transmitted.

In the first case illustrated in FIG. 13, the amount of winding P+α of the cable 40 is more than the amount of moving P of the arm 12. Therefore, tension more than necessary which exceeds the tension required for winding and is equal to or more than the biasing force of the spring 68 against the first reel 56 in the winding direction is applied to the cable 40.

In the first case, according to the radiography apparatus 10 of this embodiment, as illustrated in FIG. 11, the spring 68 is expanded by the tension applied to the cable 40, and the amount of rotation of the first reel 56 is less than the amount of rotation of the second reel 58. That is, the first reel 56 is rotated with respect to the second reel 58 in the unwinding direction of the cable 40 against the biasing force of the spring 68.

Since the amount of rotation of the first reel 56 in the winding direction is reduced, the amount of winding P of the cable 40 is equal to the amount of movement P of the arm 12, and the tension acting on the cable 40 from the first reel 56 is reduced. As a result, the application of the tension more than necessary to the cable 40 caused by the difference ΔRL between the winding perimeter RL1 of the first reel 56 and the winding perimeter RL2 of the second reel 58 is suppressed, and the concern that the cable 40 will be broken is suppressed.

Further, in the second case illustrated in FIG. 14, the amount of winding P−α of the belt 52 is less than the amount of movement P of the arm 12 due to the difference between the winding perimeter RL1 of the first reel 56 and the winding perimeter RL2 of the second reel 58, and the belt 52 is loosened.

In the second case, according to the radiography apparatus 10 of this embodiment, as illustrated in FIG. 12, the amount of rotation of the second reel 58 is more than the amount of rotation of the first reel 56 by the contraction of the spring 68. That is, the second reel 58 is rotated in the winding direction of the belt 52 by the biasing force of the spring 68 that biases the second reel 58 in the winding direction of the belt 52. Since the amount of rotation of the second reel 58 in the winding direction is increased, the amount of winding P of the belt 52 is equal to the amount of movement P of the arm 12, and the loosening of the belt 52 is suppressed. In FIG. 12, the loosening 52A of the belt 52 illustrated in FIG. 14 does not occur.

That is, according to the radiography apparatus 10 of this embodiment, the spring 68 biases the first reel 56 in the winding direction of the cable 40 and biases the second reel 58 in the winding direction of the belt 52. Therefore, the loosening of the cable 40 and the belt 52 wound around the first reel 56 and the second reel 58, respectively, is suppressed.

In addition, the spring 68 allows the difference between the amounts of rotation of the first reel 56 and the second reel 58. Therefore, the application of tension more than necessary to the cable 40 and the belt 52 caused by the difference between the winding perimeters of the first reel 56 and the second reel 58 is suppressed.

Further, the configuration in which the first reel 56 and the second reel 58 can be rotated independently is necessary as a premise for achieving the function of the spring 68. That is, for the winding direction of the cable 40 on the first reel 56 and the winding direction of the belt 52 on the second reel 58, since the rotation directions are opposite to each other, the first reel 56 and the second reel 58 need to be rotated independently. Further, the first reel 56 and the second reel 58 need to be rotated independently in order to allow the difference between the amounts of rotation of the first reel 56 and the second reel 58. The above-mentioned function can be achieved by connecting the first reel 56 and the second reel 58, which can be rotated independently, with the spring 68.

Therefore, unlike the related art, it is not necessary to perform complicated processing such as manufacturing a conical pulley having a spiral guide groove formed therein. Therefore, it is possible to more easily solve the problems caused by the difference $\Delta RL$ between the winding perimeter RL1 of the cable 40 and the winding perimeter RL2 of the belt 52, that is, the application of tension more than necessary to the cable 40 and the belt 52 and the occurrence of loosening.

Further, according to this embodiment, the first reel 56 and the second reel 58 constituting the reel unit 54 are disposed around the same rotation shaft 64, that is, coaxially. Therefore, this configuration can be simpler than the configuration in which the first reel 56 and the second reel 58 are disposed on different shafts, and it is possible to save space.

Furthermore, according to this embodiment, each of the first reel 56 and the second reel 58 is provided in the support portion 14 of the radiography apparatus 10. Since the support portion 14 is a connection portion between the arm 12 and the main body portion 16, it functions as a relay portion of the cable 40 between the arm 12 and the main body portion 16. The provision of the first reel 56 makes it easy to provide the cable 40.

In addition, since the support portion 14 is a portion serving as the base point of the arm 12 that is orbitally rotated, the support portion 14 is most suitable as a position for drawing the cable 40 and the belt 52 disposed in the outer peripheral portion of the arm 12 from the viewpoint of suppressing the complexity of the configuration. The provision of the first reel 56 and the second reel 58 at this position makes it possible to suppress the complexity of the configuration.

Further, according to this embodiment, the diameter (thickness) D1 of the cable 40 is larger than the thickness D2 of the belt 52, and the first radius E1 of the winding portion 56A of the first reel 56 in a state in which the cable 40 is not wound is smaller than the second radius E2 of the winding portion 58A of the second reel 58 in a state in which the belt 52 is not wound.

As described above, in this embodiment, the first radius E1 of the winding portion 56A of the first reel 56 for winding the cable 40 having the diameter D1 is smaller than the second radius E2 of the winding portion 58A of the second reel 58 for winding the belt 52 having the thickness D2 smaller than the diameter D1. The winding perimeter RL1 of the first reel 56 for winding the cable 40 (diameter D1) becomes larger than the winding perimeter RL2 of the belt 52 (thickness D2) of the second reel 58 as the amount of winding becomes larger.

The configuration in which the first radius E1 is set to be smaller than the second radius E2 in an initial state in which the cable 40 and the belt 52 are not wound makes it possible to suppress an excessive increase in the perimeter difference $\Delta RL$ between the winding perimeter RL1 of the cable 40 and the winding perimeter RL2 of the belt 52 in a case in which the cable 40 and the belt 52 are wound by the first reel 56 and the second reel 58, respectively.

More details are as follows. A state in which the amount of winding of the cable 40 on the first reel 56 is minimized is a state in which the arm 12 is orbitally rotated in the second direction (the direction of the arrow M2 in FIG. 12) and the first end portion 12A is moved to the maximum in the second direction. On the contrary, a state in which the amount of winding of the cable 40 on the first reel 56 is maximized is a state in which the arm 12 is orbitally rotated in the first direction and the second end portion 12B is moved to the maximum in the first direction (the direction of the arrow M1 in FIG. 11). The fact that the first radius E1 is small means that the winding perimeter RL1(1) of the cable 40 in the first turn by the first reel 56 is smaller than the winding perimeter RL2(1) of the belt 52 in the first turn by the second reel 58.

Considering a case in which the arm 12 is orbitally rotated in the first direction (the direction of the arrow M1 in FIG. 11) from the state in which the first end portion 12A is moved to the maximum in the second direction (the direction of the arrow M2 in FIG. 12), as the first radius E1 of the first reel 56 becomes smaller than the second radius E2 of the second reel 58, the amount of winding of the cable 40 on the first reel 56 becomes smaller than the amount of unwinding of the belt 52 on the second reel 58. Therefore, as the first radius E1 is smaller than the second radius E2, the tension applied to the cable 40 by the winding of the first reel 56 is more suppressed. On the other hand, the loosening of the cable 40 increases.

As described above, in a case in which the first radius E1 is smaller than the second radius E2, there is an advantage that tension more than necessary is prevented from being applied to the cable 40, but there is a disadvantage that the loosening of the cable 40 increases. However, in general, it is not preferable that tension more than necessary is applied to the cable 40 since there is a concern that the cable 40 will be broken. Therefore, the configuration in which the first radius E1 of the first reel 56 is smaller than the second radius E2 of the second reel 58 makes it possible to obtain an advantage exceeding the disadvantage that the loosening of the cable 40 increases.

In particular, according to this embodiment, the difference between the first radius E1 and the second radius E2 is equal to the difference between the diameter (thickness) D1 of the cable 40 and the thickness D2 of the belt 52. That is, in a state in which the cable 40 and the belt 52 are wound once around the first reel 56 and the second reel 58, respectively, the winding perimeter RL1 of the cable 40 and the winding perimeter RL2 of the belt 52 are equal to each other.

As described above, the maximum value of the difference ΔRL between the winding perimeter RL1 of the cable 40 and the winding perimeter RL2 of the belt 52 in a case in which the cable 40 is wound a plurality of times can be reduced by making the winding perimeter RL1(1) of the first reel 56 in a state in which the cable 40 is wound once equal to the winding perimeter RL2(1) of the second reel 58 in a state in which the belt 52 is wound once. That is, an excessive increase in the perimeter difference ΔRL between the winding perimeter RL1 of the cable 40 and the winding perimeter RL2 of the belt 52 is suppressed.

Further, according to this embodiment, the cable 40 includes the first cable 42 for applying a voltage to the radiation tube 32 of the irradiation unit 18. In general, a relatively high voltage is applied to the radiation tube 32. For this reason, the cable for applying a voltage tends to have a thick insulating coating and a large diameter. On the other hand, the thickness of the belt 52 can be reduced as long as the belt 52 can apply tension.

As described above, in a case in which the cable 40 includes the first cable 42 for applying the voltage to the radiation tube 32, the perimeter difference ΔRL between the winding perimeter RL1 of the first reel 56 and the winding perimeter RL2 of the second reel 58 tends to be large. Therefore, it is highly necessary to adopt the technology of this embodiment.

Further, the cable 40 includes the second cable 44 connected to the image receiving unit 20 in addition to the first cable 42. The first cable 42 and the second cable 44 are provided as a bundled cable group in the outer peripheral portion of the arm 12 between the first reel 56 and the first end portion 12A of the arm 12.

Then, the cable group (cable 40) is fixed in the first end portion 12A by the holding member 50. Further, the first cable 42 and the second cable 44 branch off on the side opposite to the first reel 56 with respect to the position where the cable group is fixed, and the first cable 42 is connected to the irradiation unit 18 provided in the first end portion 12A. On the other hand, the second cable 44 is provided inside the arm 12 so as to extend to the second end portion 12B and is connected to the image receiving unit 20 provided in the second end portion 12B.

As described above, the cable group (cable 40) is fixed, and the first cable 42 and the second cable 44 branch off on the side opposite to the first reel 56 with respect to the fixed position. Therefore, it is possible to prevent the tension applied to the cable group (cable 40) and the loosening of the cable group (cable 40) from affecting the first cable 42 and the second cable 44.

In addition, the cable 40 is provided as a cable group, which is a bundle of the first cables 42 and the second cables 44, in the outer peripheral portion of the arm 12 between the first reel 56 and the first end portion 12A. Therefore, the cable 40 disposed in the outer peripheral portion of the arm 12 can be aggregated in the first end portion 12A of the arm 12. As a result, it is possible to suppress the complexity of electrical wiring as compared to a case in which the cable 40 is provided in each of the first end portion 12A and the second end portion 12B in the outer peripheral portion of the arm 12.

Further, in this embodiment, the cable group (cable 40) is provided between the support portion 14 and the first end portion 12A of the arm 12 in which the irradiation unit 18 is provided. In general, in a case in which the radiography apparatus 10 is used to capture a moving image, the irradiation unit 18 is disposed below the subject H, and the image receiving unit 20 is disposed above the subject H. In many cases, a moving image is captured during surgery. In this case, it is not preferable that a portion of the arm 12 in which the cable 40 is provided is disposed above the subject H. For example, the reason is that, in a case in which the cable 40 is loosened above the subject H, the loosening may interfere with the surgery.

Here, the cable group (cable 40) is provided between the support portion 14 and the first end portion 12A which is often disposed below the subject H in the capture of a moving image. Therefore, in a case in which a moving image is captured, the portion of the arm 12 in which the cable 40 is provided can be disposed below the subject H.

Further, according to this embodiment, the other end of the belt 52 is fixed to the outer peripheral surface of the second reel 58 by the fixing member 66. This configuration in which the other end of the belt 52 is fixed to the second reel 58 makes it possible to reduce the length of the belt 52 and to suppress the complexity of the configuration of the second reel 58, as compared to, for example, a configuration in which both ends of the belt 52 are fixed to one end and the other end of the arm 12 through the second reel 58, respectively.

In addition, according to this embodiment, the belt 52 is used as the tension member. The use of the belt 52 as the tension member makes it possible to reduce the thickness of the tension member and to apply tension to the cable 40 with the tension member.

Further, according to this embodiment, the spring 68 connects the first reel 56 and the second reel 58 and is expanded and contracted in a case in which the first reel 56 and the second reel 58 are rotated in opposite directions. The spring 68 constitutes the rotational force transmission member. The use of the spring 68 as the rotational force transmission member makes it possible to bias the first reel 56 and the second reel 58 in the winding directions of the cable 40 and the belt 52, respectively, while transmitting the rotational force with a simple configuration.

In particular, according to this embodiment, the spring 68 has one end that is attached to the first pin 70A provided on the side surface of the first reel 56 and the other end that is attached to the second pin 70B provided on the side surface of the second reel 58. This configuration in which the first pin 70A and the second pin 70B, to which both ends of the spring 68 are attached, are provided on the side surface of the first reel 56 and the side surface of the second reel 58, respectively, makes it possible to attach the spring 68 to the first reel 56 and the second reel 58 with a simple configuration.

<Other Embodiments>

An example of the embodiment of the present disclosure has been described above. However, the present disclosure is not limited to the above-described embodiment, and various modifications and changes can be made without departing from the gist of the present disclosure.

For example, in the above-described embodiment, the belt 52 is used as the tension member. However, the tension member is not limited to the belt 52 as long as it can apply tension to the cable 40. However, it is preferable that the tension member has a smaller thickness than the cable 40 and that a belt or a wire is used as the tension member.

Further, in the above-described embodiment, the spring 68 is used as the rotational force transmission member. However, the rotational force transmission member is not limited to the spring 68 as long as it can transmit the rotational force of one of the first reel 56 and the second reel 58 to the other, bias the first reel 56 and the second reel 58 in the winding directions of the cable 40 and the belt 52, respectively, and allow the occurrence of the difference between the amount of rotation of the first reel 56 and the amount of rotation of the second reel 58. In addition to the spring 68, for example, a rubber member or a magnet can be used as the rotational force transmission member.

Further, in the above-described embodiment, the first reel 56 and the second reel 58 are disposed around the same rotation shaft 64. However, they may be disposed around different rotation shafts. In this case, as illustrated in FIGS. 11 and 12 for convenience of explanation, the different rotation shafts may be provided on the same axis line or may be provided on different axis lines.

Further, in the above-described embodiment, the first reel 56 and the second reel 58 are separately provided in the support portion 14 of the radiography apparatus 10. However, the first reel 56 and the second reel 58 may not necessarily be provided in the support portion 14 and may be separately provided in, for example, the main body portion 16 of the radiography apparatus 10.

Further, in the above-described embodiment, the first radius E1 of the winding portion 56A of the first reel 56 is smaller than the second radius E2 of the winding portion 58A of the second reel 58. However, the first radius E1 and the second radius E2 may be equal to each other. Furthermore, in a case in which the thickness of the tension member is larger than the diameter D1 of the cable 40, the first radius E1 of the winding portion 56A of the first reel 56 may be larger than the second radius E2 of the winding portion 58A of the second reel 58.

In addition, in the above-described embodiment, X-rays have been described as an example of the radiation. However, the radiation is not limited to the X-rays and may be, for example, γ-rays.

The disclosure of JP2019-199330 filed on Oct. 31, 2019 is incorporated herein by reference in its entirety. All of the documents, patent applications, and technical standards described in the specification are incorporated herein by references to the same extent as the incorporation of the individual documents, patent applications, and technical standards by references are described specifically and individually.

What is claimed is:

1. A radiography apparatus comprising:
   an arm that has a first end portion and a second end portion, one of which an irradiator that emits radiation is provided in and the other of which an image receiver that receives the radiation emitted from the irradiator and transmitted through a subject is attachable to, has an arc shape in a side view, and is orbitally rotatable around the subject in a posture in which the irradiator and the image receiver face each other;
   a support portion that has a track portion fitted to an outer peripheral portion of the arc shape of the arm and supports the arm to be orbitally rotatable;
   a cable that has one end electrically connected to at least one of the irradiator or the image receiver and is provided along an outer periphery of the arm from the first end portion of the arm to the support portion;
   a tension member that is used to apply tension to the cable in a case in which the arm is orbitally rotated in a first direction in which the first end portion approaches the support portion, has one end fixed to the second end portion of the arm, and is provided along the outer periphery of the arm from the second end portion to the support portion;
   a first reel that is rotated in a direction in which the cable is wound in a case in which the arm is orbitally rotated in the first direction and is rotated in a direction in which the cable is unwound in a case in which the arm is orbitally rotated in a second direction in which the second end portion approaches the support portion;
   a second reel that is rotated in a direction in which the tension member is unwound in a case in which the arm is orbitally rotated in the first direction, is rotated in a direction in which the tension member is wound in a case in which the arm is orbitally rotated in the second direction, and is provided to be independently rotatable with respect to the first reel; and
   a rotational force transmission member that, in a case in which one of the first reel and the second reel is rotated, transmits a rotational force in the same direction to the other, biases the first reel in a winding direction of the cable, biases the second reel in a winding direction of the tension member, and allows occurrence of a difference between an amount of rotation of the first reel and an amount of rotation of the second reel within a preset range in the transmission of the rotational force.

2. The radiography apparatus according to claim 1, wherein the first reel and the second reel are disposed coaxially.

3. The radiography apparatus according to claim 1, wherein the first reel and the second reel are provided in the support portion.

4. The radiography apparatus according to claim 1, wherein, in a case in which a thickness of the cable is larger than a thickness of the tension member, a first radius of a winding portion of the first reel in a state in which the cable is not wound is smaller than a second radius of a winding portion of the second reel in a state in which the tension member is not wound.

5. The radiography apparatus according to claim 4, wherein the first radius is smaller than the second radius, and a difference between the first radius and the second radius is equal to a difference between the thickness of the cable and the thickness of the tension member.

6. The radiography apparatus according to claim 1, wherein the cable includes a first cable for applying a voltage to a radiation tube of the irradiator.

7. The radiography apparatus according to claim 6, wherein the cable includes the first cable and a second cable that is connected to the image receiver,
   the first cable and the second cable are provided as a bundled cable group in an outer peripheral portion of the arm between the first reel and the first end portion, and the cable group is fixed in the first end portion, and
   the first cable and the second cable branch off on a side opposite to the first reel with respect to a position where the cable group is fixed, one of the first cable and the second cable is connected to one of the irradiator and the image receiver which is provided in the first end portion, and the other cable is provided inside the arm to extend to the second end portion and is connected to the other of the irradiator and the image receiver which is provided in the second end portion.

8. The radiography apparatus according to claim 1, wherein the irradiator is provided in the first end portion.

9. The radiography apparatus according to claim 1, wherein the other end of the tension member is fixed to the second reel.

10. The radiography apparatus according to claim 1, wherein the tension member is a belt or a wire.

11. The radiography apparatus according to claim 1, wherein the rotational force transmission member is a spring that connects the first reel and the second reel and is expanded and contracted in a case in which the first reel and the second reel are rotated in opposite directions.

12. The radiography apparatus according to claim 11, wherein the spring has one end that is attached to a first pin provided on a side surface of the first reel and the other end that is attached to a second pin provided on a side surface of the second reel.

* * * * *